US006210666B1

(12) United States Patent
Miyamura

(10) Patent No.: US 6,210,666 B1
(45) Date of Patent: Apr. 3, 2001

(54) TRUNCATED α-GALACTOSIDASE A TO TREAT FABRY DISEASE

(75) Inventor: Nobuhiro Miyamura, Kumamoto (JP)

(73) Assignee: Orphan Medical, Inc., Minnetonka, MN (US)

( * ) Notice: Subject to any disclaimer, the term of this patent is extended or adjusted under 35 U.S.C. 154(b) by 0 days.

(21) Appl. No.: 09/176,666

(22) Filed: Oct. 21, 1998

Related U.S. Application Data

(60) Provisional application No. 60/062,560, filed on Oct. 21, 1997.

(51) Int. Cl.$^7$ .............................. A61K 38/47; C12N 9/40
(52) U.S. Cl. ....................... 424/94.61; 435/200; 435/208; 530/350
(58) Field of Search ................................... 435/200, 208; 530/350; 424/94.61

(56) References Cited

U.S. PATENT DOCUMENTS

| | | | |
|---|---|---|---|
| 4,497,797 | 2/1985 | Ebata et al. | 424/118 |
| 5,179,023 | 1/1993 | Calhoun et al. | 435/320.1 |
| 5,356,804 | 10/1994 | Desnick et al. | 435/208 |
| 5,401,650 | 3/1995 | Desnick et al. | 435/208 |
| 5,658,567 | 8/1997 | Calhoun et al. | 424/94.61 |

OTHER PUBLICATIONS

Bishop, D.F., et al., "Structural organization of the human α–galactosidase A gene: Further evidence for the absence of a 3' untranslated region", *Proc. Natl. Acad. Sci. USA*, 85, pp. 3903–3907, (Jun. 1988).

Brady, R.O., et al., "Replacement Therapy For Inherited Enzyme Deficiency", *The New England Journal Of Medicine*, 289(1), pp. 9–14, (Jul. 1973).

Desnick, R.J., et al., "Fabry Disease: α–Galactosidase Deficiency", *The Metabolic Basis of Inherited Disease II, Sixth Edition*, pp. 1751–1796, (1989).

Eng, C.M., et al., "Fabry Disease: twenty–three mutations including sense and antisense CpG alterations and identification of a deletional hot–spot in the α–galactosidase A gene", *Human Molecular Genetics*, 3(10), pp. 1795–1799, (1994).

Hantzopoulos, P.A., "Molecular Cloning and Expression in E. coli of the human α–galactosidase A gene", *Dissertations Abstracts International*, 48(5), p. 1250, (Nov. 1987).

Mapes, C.A., et al., "Enzyme Replacement in Fabry's Disease, an Inborn Error of Metabolism", *Science*, 169(3949), pp. 987–989, (Sep. 1970).

Meaney, C., et al., "A nonsense mutation (R220X) in the α–galactosidase A gene detected in a female carrier of Fabry disease", *Human Molecular Genetics*, 3 (6), pp. 1019–1020, (1994).

Nagao, Y., et al., "Hypertrophic cardiomyopathy in late–onset variant of Fabry disease with high residual activity of α–galactosidase A", *Clinical Genetics*, 39, pp. 233–237, (1991).

Nakao, S., et al., "An Atypical Variant of Fabry's Disease in Men with Left Ventricular Hypertrophy", *The New England Journal of Medicine*, 333(5), pp. 288–293, (Aug. 1995).

Sakuraba, H., et al., "Identification of Point Mutations in the α–Galactosidase A Gene in Classical and Atypical Hemizygotes with Fabry Disease", *The American Journal of Human Genetics*, 47(5), pp. 784–789, (Nov. 1990).

Scheidt, W., et al., "Brief Report. An Atypical Variant Of Fabry's Disease With Manifestations Confined To The Myocardium", *New England Journal of Medicine*, 324(6), pp. 395–399, (Feb. 1991).

Bishop, D.F., et al., "Affinity Purification of α–Galactosidase A from Human Spleen, Placenta, and Plasma with Elimination of Pyrogen Contamination", *The Journal of Biological Chemistry*, 256(3), 1307–1316, (Feb. 10, 1981).

Bishop, D.F., et al., "Human α–galactosidase A: Nucleotide Sequence of a cDNA Clone Encoding the Mature Enzyme", *Proc. Natl. Acad. Sci. USA*, 83, 4859–4863, (Jul. 1986).

Calhoun, D.H., et al., "Fabry Disease: Isolation of a cDNA Clone Encoding Human α–galactosidase A", *Proc. Natl. Acad. Sci. USA*, 82, 7364–7368, (Nov. 1985).

Coppola, G., et al., "Characterization of Glycosylated and Catalytically Active Recombinant Human α–galactosidase A Using a Baculovirus Vector", *Gene*, 144, 197–203, (1994).

Desnick, R.J., et al., "Enzyme therapy in Fabry disease: Differential in vivo plasma clearance and metabolic effectiveness of plasma and splenic α–galactosidase A isozymes", *Proc. of the Nat'l Acad. of Sci. USA*, 76(10), 5326–5330, (Oct. 1979).

Goochee, C.F., et al., "Enviromental Effects on Protein Glycosylation", *Bio/Technology*, 8, 421–427, (May 1990).

Hantzopoulos, P.A., et al., "Expression of the Human α–Galactosidase A in *Escherichia Coli* K–12", *Gene*, 57, 159–169, (1987).

Luckow, V.A., et al., "Trends in the Development of Baculovirus Expression Vectors", *Bio/Technology*, 6, 47–55, (Jan. 1988).

Miller, L.K., "Baculoviruses as Gene Expression Vectors", *Ann. Rev. Microbiol.*, 42, 177–199, (1988).

Miyamura, N., et al., "A Carboxy–terminal Truncation of Human α–Galactosidase A in a Heterozygous Female with Fabry Disease and Modification of the Enzymatic Activity by the Carboxy–terminal Domain", *J. Clin. Invest., The American Society for Clinical Investigation, Inc.*, 98(8), pp. 1809–1817, (Oct. 1996).

(List continued on next page.)

*Primary Examiner*—Rebecca E. Prouty
*Assistant Examiner*—Richard Hutson
(74) *Attorney, Agent, or Firm*—Schwegman, Lundberg, Woessner & Kluth, P.A.

(57) ABSTRACT

Fabry disease results from an X-linked deficiency in the enzyme α-galactosidase A. The present invention is directed to recombinant truncated forms of α-galactosidase A, as well as therapeutic compositions comprising said truncated α-galactosidase A which are useful, for example, to treat Fabry disease patients.

4 Claims, 11 Drawing Sheets

OTHER PUBLICATIONS

Page, M.J., "p36C: An Improved Baculovirus Expression Vector for Producing High Levels of Mature Recombiant Proteins", *Nucleic Acids Research*, 17(1), 2 pp., (1989).

Quinn, M., et al., "A Genomic Clone Containing the Promoter for the Gene Encoding the Human Lysosomal Enzyme, α–Galactosidase A", *Gene*, 58, 177–188, (1987).

Tsuji, S., et al., "Signal Sequence and DNA–Mediated Expression of Human Lysosomal α–galactosidase A", *Eur. J. of Biochem.*, 165, 275–280, (1987).

| AMINO ACID | CODON |
|---|---|
| Phe | UUU, UUC |
| Ser | UCU, UCC, UCA, UCG, AGU, AGC |
| Tyr | UAU, UAC |
| Cys | UGU, UGC |
| LeU | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 1

| ORIGINAL RESIDUE | EXEMPLARY SUBSTITUTIONS | PREFFERED SUBSTITUTIONS |
|---|---|---|
| Ala (A) | val; leu; ile | val |
| Arg (R) | lys; gln; asn; | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; the; ser | phe |
| Val (V) | ile; leu; met; phe; ala; norleucine | leu |

FIG. 2

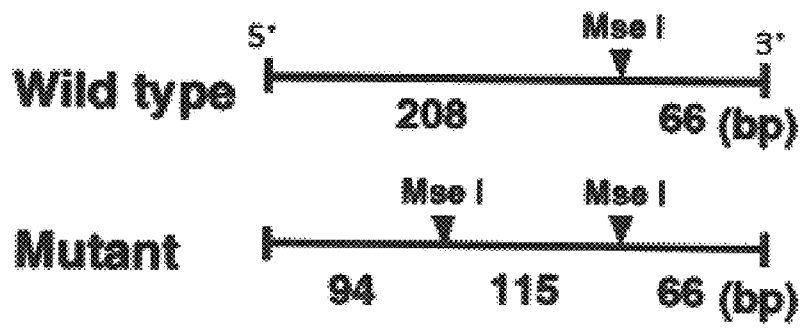
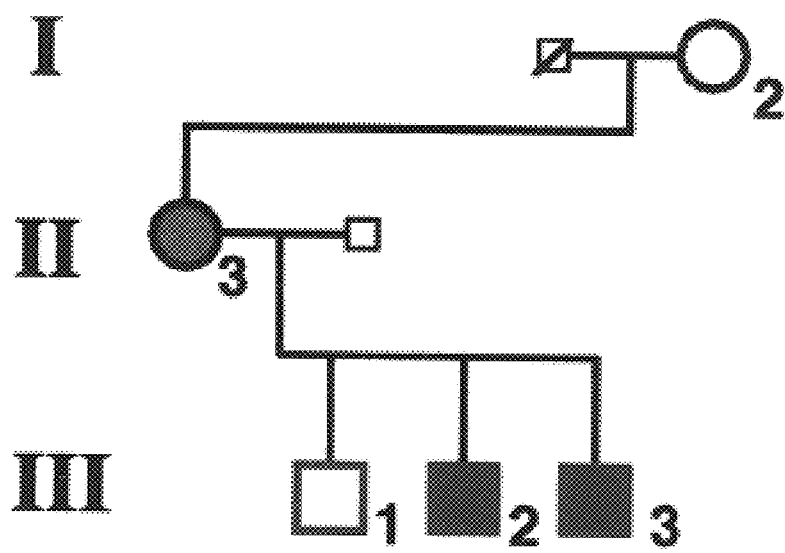
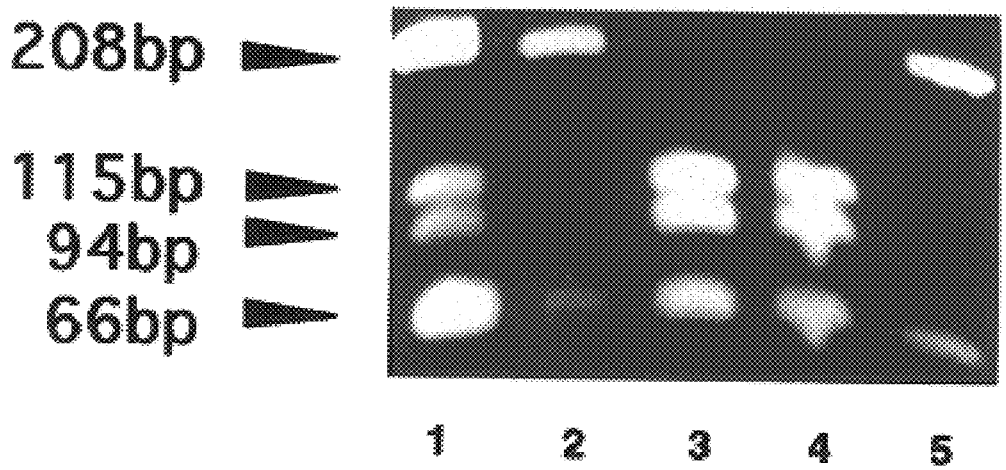
FIG. 6

TRUNCATED α-GALACTOSIDASE A TO TREAT FABRY DISEASE

This application claims the benefit under 35 U.S.C. § 119 (e) of U.S. Provisional Application No. 60/062,560 filed on Oct. 21, 1997, which is hereby incorporated by reference.

BACKGROUND OF THE INVENTION

Fabry disease is an X-linked disorder of glycosphingolipid metabolism caused by a deficiency of α-galactosidase A (α-Gal A). Human α-Gal A is a lysosomal enzyme that catalyzes the hydrolysis of α-galactosidic linkages of glycoconjugates. An X-linked inborn deficiency of this hydrolase, which is the cause of Fabry disease, leads to the accumulation of neutral glycosphingolipids, predominantly ceramide trihexoxide, primarily in the plasma and in the lysosomes of the vascular endothelium. Affected hemizygous males show various clinical symptoms, such as acroparesthesias, angiokeratoma, hypohidrosis, corneal and lenticular opacities, and progressive vascular disease of the kidney, heart, and brain, leading to death in early adulthood.

Several lines of evidence suggest that enzyme replacement therapy may be beneficial for patients with Fabry disease. For example, it has been demonstrated in cell cultures of fibroblasts obtained from patients with this disease that α-Gal A present in the culture medium is specifically transported to lysosomes. Moreover, the enzyme has been administered to patients with Fabry disease using infusions of normal plasma (Mapes et al., *Science*, 169, 987 (1970)); α-Gal A purified from placenta (Brady et al., *New Eng. J. Med.*, 279, 1163 (1973)); and α-Gal A purified from spleen or plasma (Desnick et al., *Processor. Natl. Acad. Sci. USA*, 76, 5326 (1979)). In one study (Desnick et al., supra), intravenous injection of purified enzyme resulted in a transient reduction in the plasma levels of the substrate globtriaosylceramide. However, insufficient quantities of the purified human enzyme were available for further study.

The structure of the α-Gal A gene has been determined. The 14 kb α-Gal A genomic sequence contains 7 exons encoding a 429 amino acid polypeptide, including an NH$_2$-terminal 31-residue signal peptide. Studies on unrelated families with Fabry disease have shown a variety of molecular changes in the α-Gal A gene in affected individuals. More than 70 mutations in the coding region of the α-Gal A gene have been reported, the majority of which result in a classical phenotype with no α-Gal A activity. However, a few mutations that result in single amino acid substitutions in the carboxy (C)-terminal region of α-Gal A lead to an atypical variant of Fabry disease in males, with manifestations limited to the heart (H. Sakuraba et al., *Am. J. Hum. Genet.*, 47, 784 (1990); W. V. Scheidt et al., *New Engl. J. of Med.*, 324, 394 (1991); Y. Nagao et al., *Clin. Genet.*, 39, 233 (1991); S. Nakao et al., *New Engl. J of Med.*, 333, 288 (1995)). It has been suggested that this variant type might be more common than previously believed, occurring in male patients with unexplained left ventricular hypertrophy (S. Nakao et al., *New Engl. J. of Med.*, 333, 288 (1995)).

Several mutations of the α-Gal A gene that result in the introduction of premature stop codons have also been described, including a mutant α-Gal A gene termed E398X which encodes a polypeptide that lacks 32 amino acid residues of the C-ternirus of α-Gal A. All hemizygous patients with these mutations are reported to manifest a classical phenotype (C. Meaney et al., *Hum. Mol. Genet.*, 3, 1019 (1994); M. E. Christine et al., *Hum. Mol. Genet.*, 3, 1795 (1994)). While some investigators have speculated that 26 or 28 amino acid residues from the C-terminus of α-Gal A might be proteolytically cleaved to generate the final polypeptide product present in cells (Quinn et al., *Gene*, 58, 177 (1987) and Bishop et al., *Proc. Natl. Acad. Sci. USA*, 85, 3903 (1988)), it remains uncertain whether the C-terminus of α-Gal A is necessary for enzymatic activity.

Thus, a continuing need exists for agents which have increased enzymatic activity relative to wild type α-Gal A.

SUMMARY OF THE INVENTION

The present invention provides an isolated and purified α-galactosidase A (α-Gal A) polypeptide, or a variant thereof, which has a carboxy-terminal deletion. Preferably, the truncated α-Gal A polypeptide is biologically active, and can be used to treat Fabry disease, as discussed above. As described hereinbelow, carboxy-terminal deletions of about 2 to about 10 amino acid residues of human α-Gal A unexpectedly resulted in an increase in enzyme activity relative to wild type α-Gal A polypeptide. These results indicate that the C-terminal domain of α-Gal A is important in the regulation of the activity of α-Gal A. In contrast, deletions of 12 or more amino acid residues resulted in a complete loss of enzyme activity.

A "carboxy-terminal" or "C-terminal" truncated α-Gal A polypeptide preferably refers to a polypeptide that lacks about 12, preferably about 10, and more preferably about 8 peptidyl residues, but more than 1 residue, relative to the residues at the C-terminus of native or wild type α-Gal A (SEQ ID NO:1). For example, preferred C-terminal truncated α-Gal A polypeptides include polypeptides corresponding to SEQ ID NO:3 ("Δ4"), SEQ ID NO:2 ("Δ2"), SEQ ID NO:4 ("Δ5"), SEQ ID NO:5 ("Δ6"), SEQ ID NO:6 ("Δ7"), SEQ ID NO:7 ("Δ8"), SEQ ID NO:8 ("Δ9"), and SEQ ID NO:9 ("Δ10"). Preferably, the polypeptides of the invention are biologically active.

As used herein, a "biologically active" polypeptide means that the polypeptide has an activity that is similar to or greater than, e.g., about 1.5-fold, preferably 3-fold, more preferably 4-fold, and even more preferably 6-fold, the activity of wild type α-Gal A. Methods to determine α-Gal A activity are well known to the art, see, for example, Beutler et al., *Am. J. Hum. Genet.*, 24, 235 (1972) and Mayes et al., *Clin. Chim. Acta*, 112, 247 (1981).

An isolated "variant" of a C-terminal truncated α-Gal A polypeptide is a polypeptide that has at least about 50%, preferably at least about 80%, and more preferably at least about 90%, but less than 100%, amino acid sequence homology or identity to the amino acid sequence of the corresponding wild type, preferably carboxy-terminal truncated, α-Gal A polypeptide. Thus, a variant α-Gal A polypeptide of the invention may include amino acid residues not present in the corresponding wild type α-Gal A polypeptide, and may include internal and/or amino-terminal deletions, as well as C-terminal deletions, relative to the corresponding wild type polypeptide. Variants of the invention include polypeptides having at least one D-amino acid. Preferably, the variant polypeptides of the invention are biologically active.

α-Gal A polypeptides and variants thereof which are subjected to chemical modifications, such as esterification, amidation, reduction, protection and the like, are referred to as "derivatives."

Also provided is an isolated nucleic acid molecule which encodes an α-Gal A polypeptide, or a variant thereof, which has a carboxy-terminal deletion. Preferably the isolated nucleic acid molecule further comprises a transcriptional control unit which is operably linked to the nucleic acid sequence so to provide an expression cassette.

Further provided is a therapeutic method which comprises administering to a mammal, e.g., a human, at risk of, or afflicted with, a condition associated with an α-Gal A deficiency an effective amount of a carboxy-terminal truncated form of α-Gal A or a variant thereof, which is biologically active. Preferably, the condition is Fabry disease. Also provided is a therapeutic method comprising administering to a mammal at risk of, or afflicted with, Fabry disease an effective amount of an isolated and purified nucleic acid molecule comprising a nucleic acid sequence encoding a carboxy-terminal truncated α-Gal A polypeptide.

The invention also provides an isolated and purified nucleic acid molecule comprising an α-Gal A gene having a stop codon at amino acid position 365 in α- Gal A. As described below, such a nucleic acid molecule was isolated from a family with Fabry disease. The location of the stop codon results in a 65 amino acid carboxy-terminal truncation of α-Gal A. Transfection of COS-1 cells with the mutant cDNA showed a complete loss of α-Gal A enzymatic activity. Furthermore, cells which were cotransfected with mutant and wild type cDNAs showed a lower α-Gal A activity than those with wild type alone (about 30% of wild type alone), which suggested that this mutation had a dominant negative effect on activity. Thus, the identification of a mutation that results in the truncation of an α-Gal A polypeptide at position 365 is useful in a method to identify other individuals having this particular mutation, as well as in mapping studies to determine which domains in truncated forms of α-Gal A inhibit wild type α-Gal A.

As used herein, the terms "isolated and/or purified" refer to in vitro preparation, isolation and/or purification of a nucleic acid molecule or polypeptide of the invention, so that it is not associated with in vivo substances.

BRIEF DESCRIPTION OF THE FIGURES

FIG. 1. Codons for specified amino acids.

FIG. 2. Exemplary and preferred substitutions for variant α-Gal A polypeptides.

FIG. 6. Detection of the Y365X mutation in the pedigree. Genomic DNA from individuals (symbols in FIG. 1) was amplified by PCR to obtain a 270 bp fragment including codon 365. Amplified DNA fragments were then digested with the restriction enzyme Mse I, fractionated on a 5% polyacrylamide gel, stained with ethidium bromide, and photographed under ultraviolet light. Four bands derived from normal and mutant fragments were obtained from the proband (lane 1). Three bands from the mutant fragment were obtained from the two affected sons (lanes 3 and 4), and only two bands from the normal fragment were observed in an unaffected son and the proband's mother (lanes 2 and 5).

DETAILED DESCRIPTION OF THE INVENTION

Figure 3:
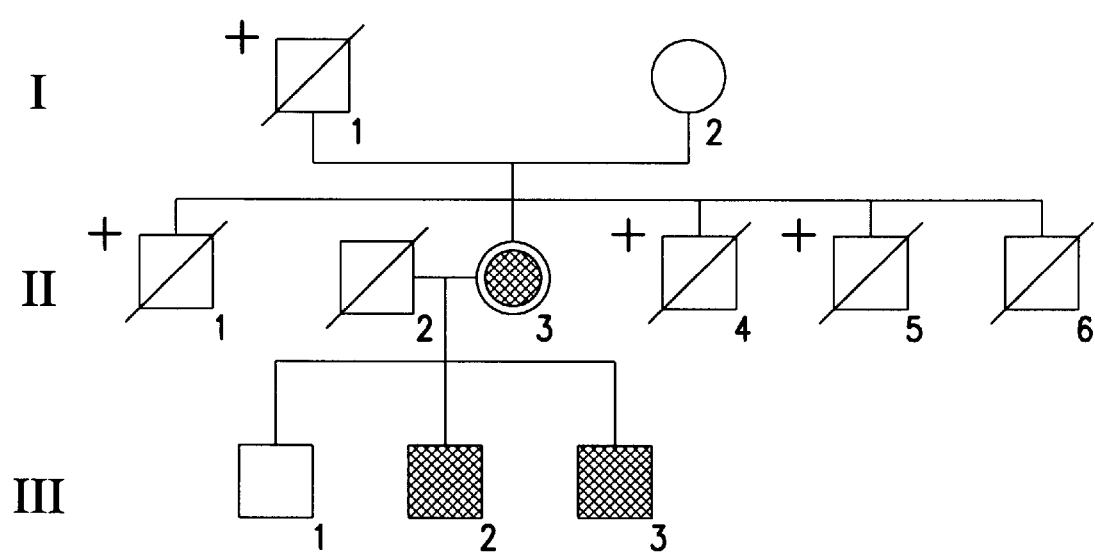
FIG. 3. Family pedigree. Males are denoted by squares, females by circles. Clinical status is indicated as follows: closed symbols, typical clinical manifestations of Fabry disease; shaded symbol, the proband; open symbols, unaffected individuals; oblique line, not examined: †, deceased; (the proband's father, deceased at age 65, was reported to have no clinical symptoms of Fabry disease).

A. Nucleic Acid Molecules of the Invention

1. Sources of the Nucleic Acid Molecules of the Invention

Sources of nucleotide sequences from which the present nucleic acid molecules encoding α-Gal A, a variant thereof or the nucleic acid complement thereof, include total or polyA+RNA from any eukaryotic, preferably mammalian, cellular source from which cDNAs can be derived by methods known in the art. Other sources of the nucleic acid molecules of the invention include genomic libraries derived from any eukaryotic cellular source. Moreover, the present nucleic acid molecules may be prepared in vitro, or by subcloning at least a portion of a DNA segment that encodes a particular α-Gal A polypeptide.

2. Isolation of a Gene Encoding α-Gal A

A nucleic acid molecule encoding an α-Gal A polypeptide can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone α-Gal A cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989). Thus, PCR-based cloning approaches rely upon conserved sequences deduced from alignments of related gene or polypeptide sequences.

Primers are made to correspond to relatively highly conserved regions of polypeptides or nucleotide sequences which were identified and compared to generate the primers, e.g., by a sequence comparison of other eukaryotic α-Gal A genes. One primer is prepared which is predicted to anneal to the antisense strand, and another primer prepared which is predicted to anneal to the sense strand, of a nucleic acid molecule which encodes α-Gal A.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone DNAs which encode α-Gal A is to screen a cDNA or genomic DNA library. Screening for DNA fragments that encode all or a portion of a DNA encoding α-Gal A can be accomplished by screening the library with a probe which has sequences that are highly conserved between genes believed to be related to α-Gal A, e.g., the homolog of α-Gal A from a different species, or by screening of plaques for binding to antibodies that specifically recognize α-Gal A. DNA fragments that bind to a probe having sequences which are related to α-Gal A, or which are immunoreactive with antibodies to α-Gal A, can be subcloned into a suitable vector and sequenced and/or used as probes to identify other DNAs encoding all or a portion of α-Gal A.

As used herein, the terms "isolated and/or purified" refer to in vitro isolation of a nucleic acid molecule or polypeptide molecule from its natural cellular environment, and from association with other components of the cell, such as nucleic acid or polypeptide, so that it can be sequenced, replicated, and/or expressed. For example, "isolated α-Gal A nucleic acid" is RNA or DNA containing greater than 7, preferably 15, and more preferably 25 or more, sequential nucleotide bases that encode at least a portion of α-Gal A, or a variant thereof, or a RNA or DNA complementary thereto, or that is complementary or hybridizes, respectively, to RNA or DNA encoding α-Gal A or a variant thereof and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated α-Gal A nucleic acid is RNA or DNA that encodes human α-Gal A and shares at least about 70%, preferably at least about 80%, and more preferably at least about 90%, sequence identity with at least a portion of the α-Gal A polypeptide having SEQ ID NO:1, e.g., a DNA molecule corresponding to SEQ ID NO.43.

As used herein, the term "recombinant nucleic acid" or "preselected nucleic acid,"e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular nucleic acid molecule.

3. Variants of the Nucleic Acid Molecules of the Invention

Nucleic acid molecules encoding amino acid sequence variants of α-Gal A are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of α-Gal A.

Oligonucleotide-mediated mutagenesis is a preferred method for preparing truncated forms, and amino acid substitution variants of α-Gal A polypeptide, including variants that are truncated. This technique is well known in the art as described by Adelman et al., *DNA*, 2, 183 (1983). Briefly, α-Gal A DNA is altered by hybridizing an oligonucleotide encoding the desired mutation to a DNA template, where the template is the single-stranded form of a plasmid or bacteriophage containing the unaltered or native DNA sequence of α-Gal A. After hybridization, a DNA polymerase is used to synthesize an entire second complementary strand of the template that will thus incorporate the oligonucleotide primer, and will code for the selected alteration in the α-Gal A DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Processor. Natl. Acad. Sci. U.S.A.*, 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989). Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the α-Gal A, and the other strand (the original template) encodes the native, unaltered sequence of α-Gal A. This heteroduplex molecule is then transformed into a suitable host cell, usually a prokaryote such as *E coli* JMI01. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for polypeptide production, generally an expression vector of the type typically employed for transformation of an appropriate host.

The method described immediately above may be modified so that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine triphosphate (dATP), deoxyriboguanosine triphosphate (dGTP), and deoxyribothymidine triphosphate (dTTP), is combined with a modified thiodeoxyribocytosine triphosphate called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM 101.

For example, a preferred embodiment of the invention is an isolated and purified DNA molecule comprising a preselected DNA segment encoding α-Gal A having SEQ ID NO:5 (a truncated form of α-Gal A which lacks the C-terminal six amino acids of wild type α-Gal A having SEQ ID NO:1) wherein the DNA segment comprises SEQ ID NO:49, or variants of SEQ ID NO:47 having nucleotide substitutions which are "silent" (see FIG. 1). That is, when silent nucleotide substitutions are present in a codon, the same amino acid is encoded by the codon with the nucleotide substitution as is encoded by the codon without the substitution. For example, valine is encoded by the codon GTT, GTC, GTA and GTG. A variant of SEQ ID NO:5 at codon 382 in the mature polypeptide (GT<u>T</u> in SEQ ID NO:47 includes the substitution of GT<u>C</u>, GT<u>A</u> or GT<u>G</u> for GT<u>T</u>. Other "silent" nucleotide substitutions in SEQ ID NO.49 which can encode α-Gal A having SEQ ID NO:5 can be ascertained by reference to FIG. 1 and page D1 in Appendix D in Sambrook et al., *Molecular Cloning: A Laboratory Manual* (1989). Nucleotide substitutions can be introduced into DNA segments by methods well known to the art, see, for example, Sambrook et al., supra. Likewise, nucleic acid molecules encoding other mammalian, preferably human, α-Gal A polypeptides may be modified in a similar manner. Moreover, the nucleic acid molecules of the invention may be modified in a similar manner so as to result in α-Gal A polypeptides that have deletions, for example, the polypeptides are truncated at the C-terminus of α-Gal A. Such deletions can be accomplished by introducing a stop codon, i.e., UAA, UAG, or UGA, in place of a codon for an amino acid.

B. Preparation of Therapeutic Agents Falling Within the Scope of the Invention

1. Nucleic Acid Molecules a. Chimeric Expression Cassettes

To prepare expression cassettes for transformation, the recombinant or preselected nucleic acid sequence or segment may be circular or linear, double-stranded or single-stranded. A preselected DNA sequence which encodes an RNA sequence that is substantially complementary to a mRNA sequence encoding α-Gal A is typically a "sense" DNA sequence cloned into a cassette in the opposite orientation (i.e., 3' to 5' rather than 5' to 3'). Generally, the preselected nucleic acid sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for α-Gal A, or portions thereof, a portion of the preselected DNA may be untranscribed, serving a regulatory or a structural function. The term "control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide or targets the polypeptide to a particular cellular location, e.g., lysosomes; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapa and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uida locus of *E. coli*, and the luciferase gene from firefly Photinus pyralis. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

b. Transformation into Host Cells

The recombinant DNA can be readily introduced into the host cells, e.g., mammalian, bacterial, yeast or insect cells, by transfection with an expression vector comprising a nucleic acid molecule of the invention, by any procedure useful for the introduction into a particular cell, e.g., physical or biological methods, to yield a transformed cell having the recombinant DNA which is preferably stably integrated into its genome, so that the nucleic acid molecules, sequences, or segments, of the present invention are expressed by the host cell.

Physical methods to introduce a preselected DNA into a host cell include calcium phosphate precipitation, lipofection, particle bombardment, microinjection, electroporation, SiC or tungsten whiskers and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, over-expressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding α-Gal A or its complement, which host cell may or may not express significant levels of autologous or "native" α-Gal A.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of α-Gal A, e.g., by immunological means (ELISAs and Western blots) or by enzymatic assays, such as the assay described hereinbelow.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected nucleic acid segment in question, they do not provide information as to whether the preselected nucleic acid segment is being expressed. Expression may be evaluated by specifically identifying the products of the introduced preselected nucleic acid sequences or evaluating the phenotypic changes brought about by the expression of the introduced preselected nucleic acid segment in the host cell.

2. Polypeptides. Variants. and Derivatives Thereof

The present isolated, purified α-Gal A polypeptides, variants or derivatives thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis*, W. H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285. These peptides or polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Purification of recombinant α-Gal A from the culture medium or the intact cells, if desired, is achieved by conventional purification means such as ammonium sulfate precipitation, column chromatography, and the like, and fractions containing the α-Gal A polypeptide can be identified by, for example, the enzymatic activity or Western blot analysis.

For example, one method to purify recombinant α-Gal A produced by a baculovirus expression vector involves harvesting the culture supernatant when the α-Gal A activity is at a peak, typically about 48 to 72 hours after viral infection of Sf9 cells. The polypeptides in the supernatant are precipitated by ammonium sulfate, dialyzed into an appropriate buffer and applied to a Concanavalin A-Sepharose (Pharmacia trademark) chromatography resin. The resin is eluted with 0.1 M α-methylglucoside to remove contaminants and then with 1 M α-methylglucoside to release the bound α-Gal A activity. After concentrating and dialyzing the eluate which contains the activity, it is applied to Sephadex G-200 or a DEAE-Sephadex A-50 (Pharmacia trademark) column. When applied to a DEAE column, the active fractions are pooled and can be further purified on a hydroxylapatite column to an estimated 95% homogeneity.

The recombinant α-Gal A produced by the baculovirus expression system, e.g., in Sf9 cells, is also characterized by glycosylation. In particular, the recombinant enzyme present in culture supernatants binds to Con-A during the purification process, which indicates the presence of α-D-glycosyl or α-D-mannosyl residues on the enzyme. Moreover, treatment of a hydroxylapatite pool obtained during purification with N-glycanase produces a marked decrease in the apparent molecular weight of the enzyme, and converts a rather diffuse band to a faster migrating and more compact band. Treatment with endoglycosidase H results in slight but reproducible changes in the migration of the enzyme in SDS gels, indicating the presence of high mannose oligosaccharide. These results are consistent with the presence of several glycoforms of the recombinant α-Gal A produced by insect cells, including both high mannose and complex type carbohydrate side chains.

In a related embodiment, the present invention also contemplates the gene fusion of α-Gal A to homologous human proteins including, but not limited to, albumin, insulin and apoprotein B. Fusions may be constructed to specific fragments of these genes that stabilize the α-Gal A and retain specific receptors for endocytosis. This technique also contemplates the genetically altered versions of the polypeptide employed where, for example, it may be advantageous to eliminate the biological activity of a portion of the fusion protein, e.g., insulin, while maintaining its intended efficacy in this context.

Once isolated and characterized, derivatives, e.g., chemically derived derivatives, of a given α-Gal A polypeptide can be readily prepared. For example, amides of α-Gal A polypeptide or variants thereof may be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of a polypeptide or polypeptide variant of the invention may be prepared in the usual manner by contacting the polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the α-Gal A polypeptide or polypeptide variants may be prepared by utilizing an N-acyl protected amino acid for the final condensation, or by acylating a protected or unprotected polypeptide. O-acyl derivatives may be prepared, for example, by acylation of a free hydroxy polypeptide or polypeptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide or polypeptide variant. Other amino-terminal modifications include aminooxypentane modifications (see Simmons et al., Science, 276, 276 (1997)).

In addition, the amino acid sequence of α-Gal A can be modified so as to result in a α-Gal A variant. The modification includes the substitution of at least one amino acid residue in the polypeptide for another amino acid residue, including substitutions which utilize the D rather than L form, as well as other well known amino acid analogs. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citrulline, a-methyl-alanine, para-benzoyl-phenylalanine, phenylglycine, propargylglycine, sarcosine, and tert-butylglycine.

One or more of the residues of the polypeptide can be altered, preferably so long as the polypeptide variant is biologically active. For example, for α-Gal A variants, it is preferred that the variant has a similar, if not greater, biological activity than that of the corresponding non-variant wild type polypeptide, e.g., a polypeptide having SEQ ID NO:1. Conservative amino acid substitutions are preferred-- that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions are shown in FIG. 2 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the polypeptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic; trp, tyr, phe.

The invention also envisions polypeptide variants with non-conservative substitutions. Non-conservative substitutions entail exchanging a member of one of the classes described above for another.

Acid addition salts of the polypeptide or variant polypeptide or of amino residues of the polypeptide or variant polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

Moreover, it is also envisioned that the agents of the invention, e.g., α-Gal A polypeptides, are modified in a manner that increases their stability in vivo, i.e., their bioavailability. These modified agents are termed "derivatives." Methods to prepare such derivatives are well known to the art.

C. Formulations. Dosages and Routes of Administration of the Therapeutic Agents of the Invention Homogeneous preparations of the nucleic acid or polypeptide molecules of the invention are particularly useful for enzyme replacement therapy of Fabry disease and any other disease which results from a deficiency of α-Gal A. Recombinant production of the α-Gal A polypeptide of the invention provides a plentiful source of active enzyme. Thus, an effective amount of recombinant α-Gal A of the invention or a biologically active variant, fragment, e.g., ac-terminal truncated from of α-Gal A or derivative thereof is administered to a mammal for a time and under conditions sufficient to treat the deficiency by increasing enzyme level.

A therapeutically effective amount of recombinant α-Gal A may range from about 50 to about 10,000 units of enzyme activity per kg body weight per day. A unit of α-Gal A activity is as defined in Calhoun et al., Proc. Natl. Acad. Sci. USA, 82, 7364 (1985) with one unit corresponding to one nanomole of 4-methylumbelliferyl-α-D-galactopyranoside hydrolyzed per hour at 37° C.

For example, the uptake of recombinant α-Gal A in normal and Fabry fibroblasts can be examined to show that the recombinantly produced enzyme restores α-Gal A activity in cells lacking the enzyme. Restoration of function can be tested by addition of the purified enzyme to the culture medium (see Mayes et al., Am. J. Hum. Genet., 34, 602–610 (1982)), which is taken up in a dose dependent fashion so as to produce an increase in enzyme levels in normal and in Fabry fibroblasts.

Accordingly, the subject invention contemplates treating Fabry disease or other diseases resulting from a deficiency of α-Gal A in mammals by administering a pharmaceutical composition containing a pharmaceutically effective amount of an α-Gal A polypeptide of the invention, a variant, or a derivative thereof. Additionally, a method for treating Fabry disease (or other diseases characterized by this enzyme deficiency) in a mammal is contemplated in which a nucleic acid molecule encoding an α-Gal A polypeptide of the invention is introduced into a cell in such a manner that said nucleic acid molecule is expressed intracellularly. Such expression may be extrachromosomal in said cell or occur following integration into the genome of said cell. In this case where the enzyme is introduced into the cell via a nucleic acid, the nucleic acid molecule may be carried to the cell and transferred into said cell by a second nucleic acid molecule (e.g., various viruses). Moreover, administration of sense or antisense nucleic acid molecules of the invention may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., *Immunity*, 3, 165 (1995); Stevenson et al., *Immunol. Rev.*, 145, 211 (1995); Molling, *J. Mol. Med.*, 75, 242 (1997); Donnelly et al., *Ann. N.Y. Acad. Sci.*, 772, 40 (1995); Yang et al., *Mol. Med. Today*, 2, 476 (1996); Abdallah et al., *Biol. Cell*, 85, 1 (1995)). Pharmaceutical formulations, dosages and routes of administration for nucleic acids are generally disclosed, for example, in Felgner et al., supra.

The active ingredients of the pharmaceutical compositions comprising recombinant α-Gal A are contemplated to exhibit excellent and effective therapeutic activity in replacing the enzymatic deficiency found in Fabry disease or other conditions resulting from this deficiency. Thus, the active ingredients of the therapeutic compositions of the invention exhibit enzymatic activity when administered in therapeutic amounts from, for example, about 0.1 μg to about 2000 μg of polypeptide per kg of body weight per day. The dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular, intravenous, intranasal, intradermal, subcutaneous, or suppository routes. The compound or compounds can also be administered by inhalation or insufflation. Depending on the route of administration, the active ingredients of recombinant α-Gal A-containing pharmaceutical composition may be required to be coated in a material to protect said ingredients from the action of enzymes, acids or other natural conditions.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Coatings for α-Gal A preparations are useful to reduce degradation of the enzyme when administered as a therapeutic agent. Coatings also reduce the immunogenicity of the enzyme to help prevent undesirable side effects of administering such a therapeutic agent. A particularly useful coating to provide these characteristics is a polyethylene glycol.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When recombinant α-Gal A is suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparation should contain at least 1% of active compound. The percentage of the compositions and preparations may, of course, be varied and may conveniently be between about 5 to about 80% of the weight of the unit. The amount of active compound in such therapeutically useful compositions is such that a suitable dosage is obtained. Preferred compositions or preparations according to the present invention are prepared so that an oral unit dosage form contains between about 10 μg and 1000 μg of active compound.

The tablets, troches, pills, capsules and the like may also contain the following: A binder such as gum agragacanth, acacia, corn starch or gelatin; excipients such as dicalcium phosphate; a disintegrating agent such as corn starch, potato starch, alginic acid and the like; a lubricant such as magnesium stearate; a sweetening agent such as sucrose, lactose or saccharin or a flavoring agent such as peppermint, oil of wintergreen, or cherry flavoring. When the dosage form is a capsule, it may contain, in addition to materials of the above type, a liquid carrier. Various other materials may be present as coatings or to otherwise modify the physical form of the unit dosage. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Unit dosage form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health impaired as herein disclosed in detail.

The principal active ingredient, especially, recombinant α-Gal A, is compounded for convenient and effective administration in pharmaceutically effective amounts with a suitable pharmaceutically acceptable carrier in dosage unit form as hereinbefore disclosed. A unit dosage form can, for example, contain the principal active compound in amounts ranging from 10 µg to about 1000 µg. Expressed in proportions, the active compound is generally present in from about 10 µg to about 1000 µg/ml of carrier. In the case of compositions containing supplementary active ingredients, the dosages are determined by reference to the usual dose and manner of administration of the said ingredients.

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The invention will be further described by the following example.

EXAMPLE 1

Methods

Subjects. The proband, a 52-year old Japanese female (II-3), with typical manifestations of Fabry disease except for angiokeratoma, and her kindred were studied (see FIG. 3). Informed consent was obtained from each subject.

Enzyme sources, enzyme assay, andprotein determination. Lymphocytes were separated from heparinized blood with Lymphoprep® (Daiichi Pure Chemicals, Tokyo, Japan). COS-1 cells transfected with wild type or various mutant α-Gal A cDNAs were collected from culture dishes and lysed in PBS by three cycles of freezing and thawing. The lysates were assayed for α-Gal A activity with 4-methylumbelliferyl α-galactoside as substrate and N-acetylgalactosamine (Sigma Chemical Co., St. Louis, Mo.) as α-Gal B inhibitor, according to the method of Beutler et al. (*Am. J. Hum. Genet.*, 24, 237 (1972)) and Mayes et al., (*Clin. Chim. Acta.*, 112, 247 (1981)). Protein concentration was determined by the method of Bradford (M. M. Bradford, *Anal. Biochem.*, 72, 248 (1976)) with Coomassie Protein Assay Reagent (Pierce Chemical Co., Rockford, Ill).

Identification of the α-Gal A mutation. Genomic DNA was isolated from peripheral blood lymphocytes (M. Gross-Ballard et al., *Eur. J. Biochem.*, 36, 32 (1973)). Each of the seven exons of the α-Gal A gene was amplified by PCR (R. K. Saiki et al., *Science*, 239, 487 (1988)), using seven primer sets designed to amplify human α-Gal A gene sequences (R. Kornreich et al., *Nucl. Acids Res.*, 17, 3301 (1989)) (Table 3). PCR amplification with 500 ng of genomic DNA was carried out using 100 pmol of each primer, 2.5 mmol/liter of dNTPs and 2.5 U of Ampli Taq DNA polymerase (Perkin Elmer/Cetus, Norwalk, Conn.) in 100 µl of reaction mixture containing PCR buffer (10 mmol/liter Tris pH 8.3, 50 mmol/liter KCl, 1.5 mmol/liter $MgCl_2$, 0.001% gelatin) using a thermal cycle programmer (Model 300; Astee, Fukuoka, Japan) and the following cycling parameters: 94° C. for 1 minute, 58° C. for 1 minute, and 74° C. for 2 minutes, for 30 cycles. PCR products were purified using Suprec® (Takara Shuzo Co., Ltd., Kyoto, Japan).

All coding regions and exon-intron junctions of the amplified DNA fragments were directly sequenced according to the snap cooling method (N. Kusukawa et al., *Biotechniques*, 9, 66 (1990)), using 0.5–1 µg of amplified fragment as the template, and/or sequenced after subcloning into pUC19 by standard methodologies (F. Sanger et al., *Processor. Natl. Acad. Sci. USA*, 74 5463 (1977)), using Sequenase version 2.0 DNA sequencing kits (United States Biochemical Company, Cleveland, Ohio). If fragments were sequenced after subcloning, multiple clones were sequenced to obtain the sequence.

Reverse transcription polymerase chain reaction (RT-PCR)-direct sequencing analysis of α-Gal A mRNA. To analyze α-Gal A gene expression in the heterozygous subject (11-3, FIG. 3), direct sequencing of the RT-PCR (M. A. Frohman et al., *Processor. Natl. Acad. Sci. USA*, 86, 8998 (1988)) products was performed from skin fibroblasts isolated from the forearms of the subject. The fibroblasts were cultured in MEM supplemented with 10% FBS in an atmosphere of 5% $CO_2$ and 95% air in 10 cm culture dishes. Total RNA was isolated from the cells using Isogen® (Nippon Gene Co., Ltd., Tokyo, Japan). After treatment with DNAase (RNase free) (Sigma) at 37° C. for 60 minutes in DNAase buffer (0.1 mmol/liter sodium acetate, 5 mmol/liter $MnCl_2$), 3 µg of total RNA was reverse transcribed into cDNA with 50 pmol of oligo(dT)$_{17}$, 20 mmol/liter of dNTPs, and 50 U of RNase inhibitor (Promega, Madison, Wis.) using 12.5 U of Avian myeloblastosis or Moloney murine leukemia virus reverse transcriptase (Takara Shuzo Co., Ltd., Kyoto, Japan) in reverse transcriptase buffer (50 mmol/liter Tris pH 8.3, 50 mmol/liter KCl, 8 mmol/liter $MgCl_2$, 5 mmol/liter DTT) at 42° C. for 120 minutes. The sample was then heated to 98° C. for 10 minutes, and immediately chilled on ice.

For PCR amplification of α-Gal A cDNA, a sense primer 5'-ATT-GTTGATGTTGCTGGACCAG-3' (nt 753–774; P. Lemanski et al., *J. Biol. Chem.*, 262, 2062 (1986); SEQ ID NO:13) and an antisense primer 5'-GTCTTTTAATGACATCTGCATT-3' (nt 1260–1281; SEQ ID NO: 14) were prepared. These primers span exon 5 to 7. PCR amplification was carried out using one-tenth of the total reverse transcription mixture as described above. The PCR products were directly sequenced as described above.

Detection of the Y365X mutation in the pedigree. For rapid screening of the mutation identified in the proband, which creates a novel MseI restriction site at nt 1095, genomic DNA from the family members were examined by polymerase chain reaction-restriction fragment length polymorphism (PCR-RFLP) analysis. A primer pair (a sense primer, 5'-GAGACAACTTTGAAGTGAAGTGTGG-3' (nt 1001–1020; SEQ ID NO:15) and an antisense primer, 5'-AATGACATCTGCATTGTATTTTC-3' (nt 1274–1252; SEQ ID NO:16) was used for amplification, under the same PCR conditions as described above, using 500 ng of genomic DNA as the template. Amplified DNA fragments were then digested in a 15 µl reaction mixture containing 10 µl of the PCR product, 1.5 µl of 10 ×NEB2 buffer, and 10 U of the restriction enzyme MseI (New England Biolab, Beverly, Mass.). The fragments were then fractionated in a 5% acrylamide gel (8 cm×6 cm×0.5 cm, acrylamide; N,N'-methylene-bis-acrylamide=19:1) and photographed under ultraviolet light after staining with ethidium bromide.

Cloning the mutant α-Gal A cDNA and construction of the expression plasmid. Two overlapping α-Gal A cDNA fragments, one 851 bp fragment covering nt 1–851, and another 998 bp fragment covering nt 299–1296, both with an additional EcoRI site and HindIII site at the 5' and 3' end, respectively, were synthesized by RT-PCR using 3 µg of total RNA prepared from cultured fibroblasts either from an affected or an unaffected hemizygote. Each amplified fragment was isolated and cleaved with EcoRI and HindIII, and ligated into the EcoRI-HindIII site of pUC19. The sequence of each fragment was confirmed as described above. The plasmid containing the 851 bp fragment was digested with EcoRI and BglII, and the resultant 520 bp fragment was inserted into the EcoRI-BglII site of pCMV. The plasmid containing the 998 bp fragment was digested with BglII and HindIII, and the resultant 788 bp fragment was ligated to the BglII-HindIII site of pCMV, into which had previously been inserted the 520 bp EcoRI-BglII-fragment. The plasmids having a 1.3 kb fragment encoding the mutant of wild type α-Gal A were designated pCMV-AGK (for α-Gal A Kumamoto) or pCMV-AGW (for α-Gal A wild type), respectively.

TABLE 1

| No. | Sequence | Orientation | Genomic* Coordinates |
|---|---|---|---|
| 1 | 5'-AATAAGTCATCGGTGATTGGTCCGC-3'; SEQ ID NO:17 | Sense | 1090 to 1114 |
| 2 | 5'-AAGGGAAGGGAGTACCCAATATCTG-3'; SEQ ID NO:18 | Antisense | 1378 to 1402 |
| 3 | 5'-CCCAAGGTGCCTAATAAATGGGAGG-3'; SEQ ID NO:19 | Sense | 5016 to 5040 |
| 4 | 5'-GCTTACAGTCCTCTGAATGAACAAG-3'; SEQ ID NO:20 | Antisense | 5289 to 5313 |
| 5 | 5'-GGTGACTCTTTTCCTCCCTCTCATT-3'; SEQ ID NO:21 | Sense | 7240 to 7264 |
| 6 | 5'-CCTTTGTGGCTAAATCTCTGGAATG-3'; SEQ ID NO:22 | Antisense | 7456 to 7480 |
| 7 | 5'-GCCCCAGCTGGAAATTCATTTCTTT-3'; SEQ ID NO:23 | Sense | 8265 to 8289 |
| 8 | 5'-ACAGTTCTATTGGATTCTGGGCTCAC-3'; SEQ ID NO:24 | Antisense | 8421 to 8445 |
| 9 | 5'-GAGAAGGCTACAAGTGCCTCCTTTA-3'; SEQ ID NO:25 | Sense | 10041 to 10065 |
| 10 | 5'-ATAGGAAACAAGCCTACCGCAGGGT-3'; SEQ ID NO:26 | Antisense | 10321 to 10345 |
| 11 | 5'-GGTTTCTCCATATGGGTCATCTAGG-3'; SEQ ID NO:27 | Sense | 10429 to 10453 |
| 12 | 5'-GGCCCAAGACAAAGTTGGTATTGGG-3'; SEQ ID NO:28 | Antisense | 10745 to 10769 |
| 13 | 5'-CAGGGCCACTTATCACTAGTTGCTA-3'; SEQ ID NO:29 | Sense | 10926 to 10950 |
| 14 | 5'-GGTGGACAGGAAGTAGTAGTTGGCA-3'; SEQ ID NO:30 | Antisense | 11283 to 11307 |

*The nucleotide coordinates for genomic sequences are those described in R. Kornreich et al., Nucl. Acids Res., 17, 3301 (1989).

TABLE 2

| Mutation | Sequence | | cDNA Coordinates |
|---|---|---|---|
| pCMV-AGΔ2 | 5'-TT<u>AAGCT</u><u>TCA</u>GTCTTTTAATGAC-3'; | SEQ ID NO:31 | 1266 to 1288 |
| pCMV-AGΔ4 | 5'-<u>GT</u>AAGCTT<u>TA</u>TAATGACATCTGC-3'; | SEQ ID NO:32 | 1260 to 1281 |
| pCMV-AGΔ5 | 5'-<u>T</u>AAGCTTTT<u>TA</u>TGACATCTGCATTGT-3'; | SEQ ID NO:33 | 1255 to 1280 |
| pCMV-AGΔ6 | 5'-TA<u>AA</u>GCTTTTAAT<u>TA</u>CATCTGCAT-3'; | SEQ ID NO:34 | 1258 to 1281 |
| PCMV-AGΔ7 | 5'-TA<u>AA</u>GCTTTTAATGAC<u>TA</u>CTGCAT-3'; | SEQ ID NO:35 | 1258 to 1281 |
| pCMV-AGΔ8 | 5'-TA<u>AA</u>GCTTTTAATGACAT<u>CTA</u>CATTGT-3'; | SEQ ID NO:36 | 1255 to 1281 |
| PCMV-AGΔ9 | 5'-TT<u>AAGCTT</u>ATCTGC<u>TA</u>TGTATTTTC-3'; | SEQ ID NO:37 | 1249 to 1275 |
| pCMV-AGΔ10 | 5'-CAT<u>AA</u>GCTTT<u>CA</u>ATTTTCTAGCTGAAGC-3'; | SEQ ID NO:38 | 1239 to 1266 |
| pCMV-AGΔ11 | 5'-CAT<u>AA</u>GCTTTGT<u>CTA</u>TTCTAGCTGAAGC-3'; | SEQ ID NO:39 | 1239 to 1266 |
| pCMV-AGΔ12 | 5'-<u>GC</u>AAGCTTTT<u>A</u>TAGCTGAAGCAAAAC-3'; | SEQ ID NO:40 | 1234 to 1259 |
| pCMV-AGΔ17 | 5'-<u>CTGA</u>AGCTTAAACAGTGCCTGTGGG-3'; | SEQ ID NO:41 | 1219 to 1243 |

Oligonucleotide sequences are those of the antisense strand of the carboxy-terminal region of α-Gal A cDNA as numbered for sequences of full length cDNA (P. Lemanski et al., supra). Deviations from the wild-type sequence are underlined. Stop codons are indicated in boldface. HindIII sites are present at the 5'-end.

Construction of mutant α-Gal A cDNAs. Eleven sets of primer pairs with a sense primer (5'-CAAGGGTACCAGCTTAGACAGG-3'(nt 979–1000; SEQ ID NO:42) with a KpnI site at nt 985, and antisense primers, which were modified to create terminating codons at various C-terminal sites and to have an additional HindIII site (Table 2), were used together to generate PCR fragments using 5 ng of pCMV-AGW as the template. Each fragment generated with each primer pair (sized 258 to about 303 bp) was digested with KpnI and HindIII, and inserted into the corresponding KpnI-HindIII site of pCMV-AGW. The resulting plasmids which encode α-Gal A with C-terminal deletions of 2, 4, 5, 6, 7, 8, 9, 10, 11, 12, and 17 amino acid residues were designated pCMV-AGΔ2, pCMV-AGΔ4, pCMV-AGΔ5, pCMV-AGΔ6, pCMV-AGΔ7, pCMV-AGΔ8, pCMV-AGΔ9, pCMV-AGΔ10, pCMV-AGΔ11, pCMV-AGΔ12, and pCMV-AGΔ17, respectively. To eliminate any possible PCR error, the entire coding regions of the cDNAs were sequenced before transfection.

Expression of α-Gal A mutants in COS-1 cells. COS-1 cells were grown at 37° C. in Dulbecco's modified Eagle's medium supplemented with 10% FBS in an atmosphere of 5% $CO_2$ and 95% air to a density of 50% in 10 cm culture dishes. Cells were collected, washed three times with PBS, and separated into aliquots of $5 \times 10^8$ cells in 0.7 ml of modified PBS containing 30.8 mM NaCl, 120.7 mM KCl, 8.1 mM $Na_2HPO_4$, 1.46 mM $KH_2PO_4$, and 10 mM $MgCl_2$, and used for transfection. Transfections were performed with 10 µg of each plasmid for each experiment using electroporation according to the manufacturer's instructions (Gene Pulser Transfection Apparatus, Bio-Rad Laboratories, Richmond, Calif.). The conditions employed for electroporation were either 300 V and 500 µF with a time constant of 14.2±0.5 ms or 280 V and 250 µF with a time constant of 8.1±0.35 ms. Independent transfections were performed three or four times for each plasmid. After transfection, each sample was separated into two 10 cm culture dishes and grown as described above. The medium was aspirated 12 hours after transfection, and after a wash with PBS, new medium was added. Cells were harvested from one of two dishes per transfection after 72 hours, lysed by three cycles of freezing and thawing in PBS, and α-Gal A activity measured as described above. Cells from the second dish were harvested for RNA preparation. Total RNA was isolated from the cells using Isogen® for Northern blot analysis.

Analysis of α-Gal A mRNA. Northern blot analysis was performed by standard procedures (Sanbrook et al., *Molecular Cloning: A Laboratory Manual*, Cold Spring Harbor Laboratory, Cold Spring Harbor, N.Y. (1989)). Three to ten µg of total RNA was size-fractionated by agarose-gel electrophoresis, blotted onto a nitrocellulose membrane, and hybridized for 12 hours with cDNA probes labeled by the random primer method. Two cDNA probes were used for hybridization. The first probe was a 1.3 kb EcoRI-HindIII fragment of α-Gal A cDNA prepared from the expression plasmid pCMV-AGW. After hybridization, membranes were washed twice with 0.1×SSC with 0.1% SDS at 60° C. for 30 minutes and exposed to Imaging Plate® (Fuji Film Co., Ltd., Tokyo, Japan) and/or x-ray film for an appropriate time. Membranes were then washed with 5×SSC, 5×Denhardt's, 50% formamide, with 0.1% SDS at 70° C. for 2 hours and rehybridized with the second probe, a 400 bp fragment of β-actin cDNA (Nippon Gene Co., Ltd.) as an internal control for normalization of the transfection efficiency. Radioactivity was measured using a Bio Image-Analyzer BA100® (Fuji Film Co., Ltd.).

Statistical analysis. Statistical analysis was performed using the nonpaired Student's r test. Results are given as mean±SD.

Results

Clinical data. A 52-year old female (FIG. 3, II-3) visited a hospital complaining of chest pain and occasional breathlessness since the age of 40, accompanied by periodic crises of severe pain in the extremities, and hypohidrosis since the age of 11 (Table 3). On suspicion of hypertrophic cardiomyopathy, myocardial biopsy was performed, which revealed marked vacuolar degeneration. She was admitted for further examination. Upon physical examination, she had mild hypertension. Cardiac auscultation revealed a moderate systolic murmur. Slit-lamp examination revealed corneal opacities and tortuous retinal vessels. Electrocardiographic abnormality, and mild cardiomegaly on x-ray film were observed. Angiokeratoma was not present. Hematogram, blood chemistry and other routine laboratory examinations revealed no abnormality except for proteinuria of 0.4–0.8 g per d. Two of the patient's three sons (FIG. 3, III-2 and III-3) showed almost the same clinical symptoms, and both had angiokeratoma. In addition, the second son (III-2) had had an episode of slight bleeding in the midbrain at 28 years of age, and the third son (III-3) had been undergoing hemodialysis since the age of 26 because of uremia (Table 1). The proband's mother (I-2) and first son (III-1) were clinically normal and the father (I-1), though not examined because of death due to an unknown cause at 65 years of age, was considered to be normal according to information from family members. Assays of α-Gal A in lymphocytes revealed partial deficiency of enzymatic activity in the proband (24.5 nmol/h/mg protein), and severe deficiency in two affected sons (0.7 and 0.9 nmol/h/mg protein, respectively).

TABLE 3

|  | Heterozygote II-3 | Hemizygote 1 III-2 | Hemizygote 2 III-3 |
|---|---|---|---|
| Age | 58 | 34 | 29 |
| Acroparesthesia | Since childhood | Since childhood | Since childhood |
| Hypohidrosis | Moderate | Moderate | Severe |
| Corneal Dystrophy | + | − | n.d. |
| Angiokeratoma | − | Since adolescence | Since adolescence |
| Hypertension | + | − | + |
| Cardiomyopathy | + | + | + |
| Proteinuria | Mild | Mild | Severe |
| Creatinine clearance (ml/min) | 60.8 | 51.2 | <5 |
| Brain vascular disease | − | + | − |
| Lymphocyte α-Gal A activity (nmol/h per mg protein) | 24.5 | 0.7 | 0.9 | n.d. not determined.

Figure 4:
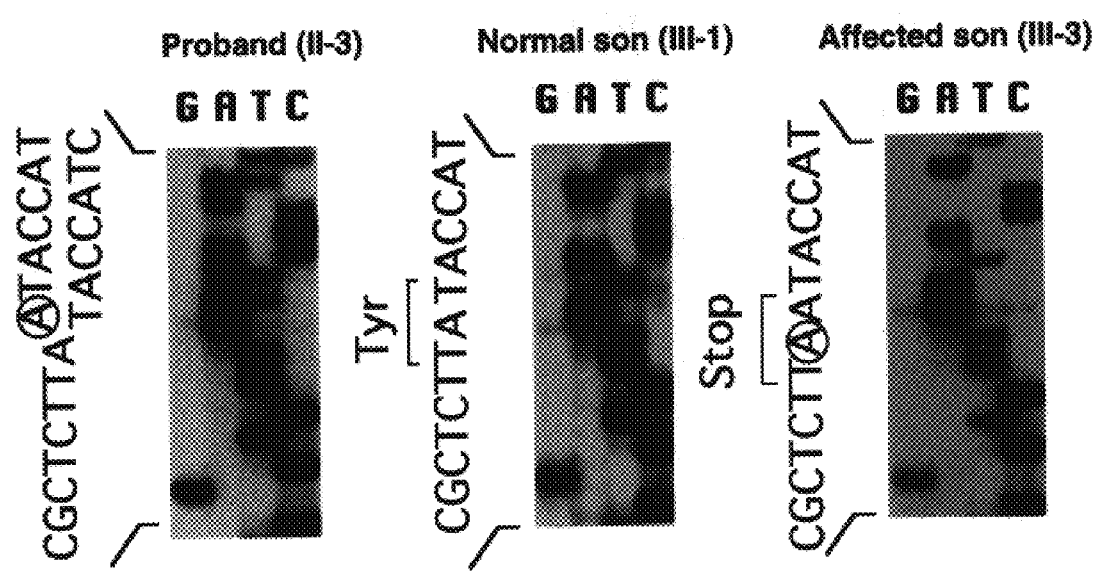
FIG. 4. Sequence analysis of the α-Gal A gene of family members. Polymerase chain reaction (PCR) products from the genomic DNAs of subjects II-3, III-2, and III-3 in FIG. 1 were directly sequenced. The nucleotide inserted at position 1095 in exon 7 is indicated by the circle. This insertion results in a stop codon at position 365 in the α-Gal A polypeptide.

Identification of the α-Gal A mutation. Direct nucleotide sequencing of the PCR products from genomic DNA of the affected individuals (proband and two sons) revealed an adenine nucleotide insertion at nt 1095 in exon 7 of the coding sequence, which resulted in a tyrosine-to-stop codon substitution at amino acid residue 365 (Y365X), causing a C-terminal truncation by 65 amino acid residues (FIG. 4). Because of the presence of the insertion in one allele and the absence in the other, overlapping bands were observed after nt 1096 on sequence analysis of the proband.

Figure 5:
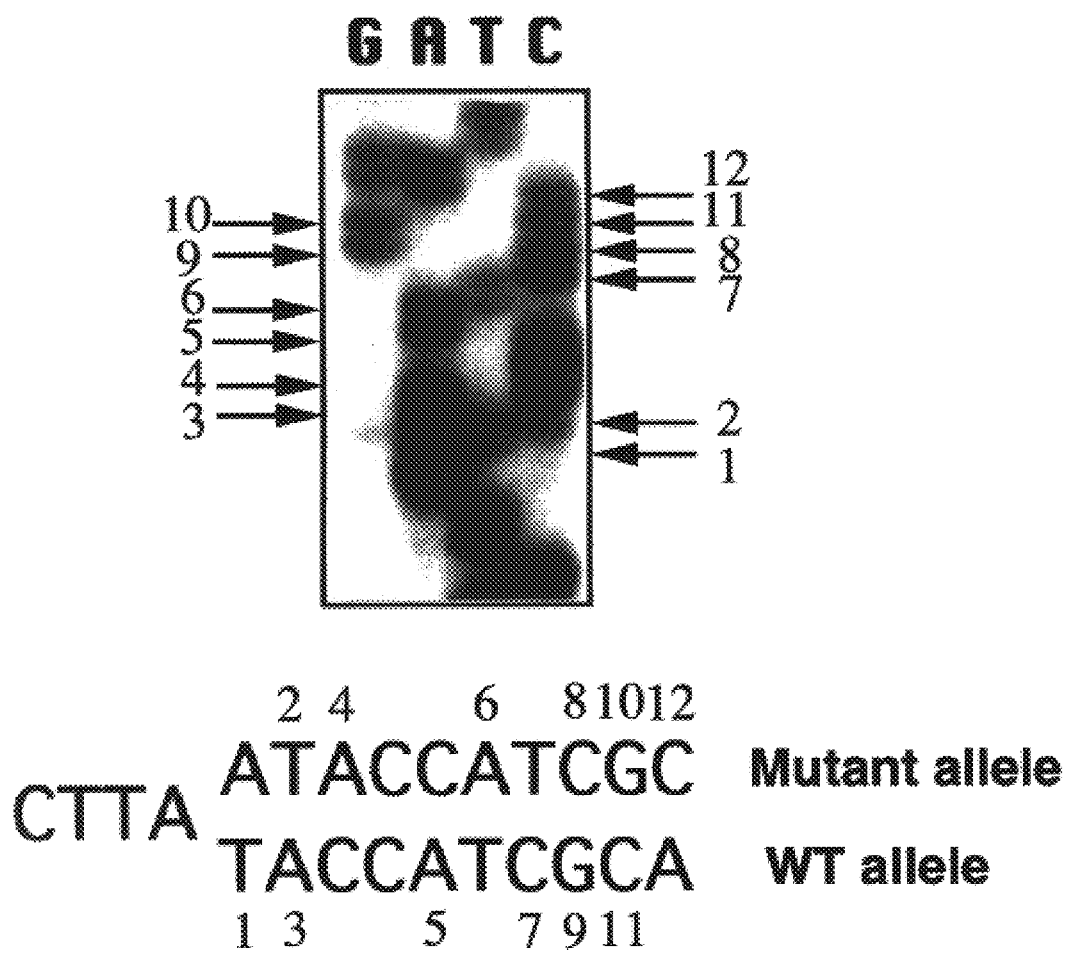
FIG. 5. Analysis of expression of wild type and mutant α-Gal A genes in a heterozygote. The amplified product from the proband's cDNA (obtained from RNA isolated from cultured fibroblasts of the proband) was directly sequenced. Bands 1, 3, 5, 7, 9, and 11 are extension products from the transcript of wild-type α-Gal A mRNA, while bands 2, 4, 6, 8, 10, and 12 are extension products of the mutant α-Gal A mRNA.

RT-PCR-direct sequencing analysis of α-Gal A mRNA. Transcription of the Y365X mutation into mRNA was confirmed by RT-PCR analysis of RNA obtained from the hemizygous males (III-2 and III-3). In RT-PCR-direct sequence analysis of cultured fibroblasts from the heterozygous female (II-3), overlapping bands were observed after nt 1096 (FIG. 5). Corresponding bands derived from mRNA transcribed from the wild type or the mutant alleles showed almost the same densities as those observed in genomic PCR direct sequencing (FIG. 4). Assuming that the density of each band in direct sequence analysis corresponded to the amount of each template (i.e., RT-PCR product), and that the amount of each RT-PCR product was consistent with the amount of mRNA transcribed from each allele, this finding suggested that there was no difference between the amounts of mRNAs transcribed from the wild type and the mutant allele (compare bands 1 and 2; 3 and 4; 5 and 6; 7 and 8; 9 and 10; and 11 and 12; respectively, in FIG. 5).

Detection of the Y365X mutation in the pedigree. In order to identify the Y365X mutation in the members of the family, PCR-RFLP analysis was performed. Two bands of 208 and 66 bp were observed for the proband's mother and the unaffected son, three bands of 115, 94, and 66 bp for two sons, and four bands of 208, 115, 94, and 66 bp for the proband (FIG. 6). Therefore, two affected sons (III-2 and III-3, respectively, in FIG. 3) were hemizygous, and the proband (II-3) was heterozygous for the mutation. Although the proband's mother (I-2) had been expected to be an asymptomatic heterozygote by pedigree analysis (FIG. 3), both she and the unaffected son (III-1) were shown to be normal. The proband's mother's genomic DNA was directly sequenced and it was confirmed that there was no mutation at codon 365. This implied that this was a de novo mutation, which had occurred in the germ line of either of the proband's parents, although the data do not exclude the possibility that the proband's father was an asymptomatic or a mildly symptomatic hemizygote.

Figure 7A:
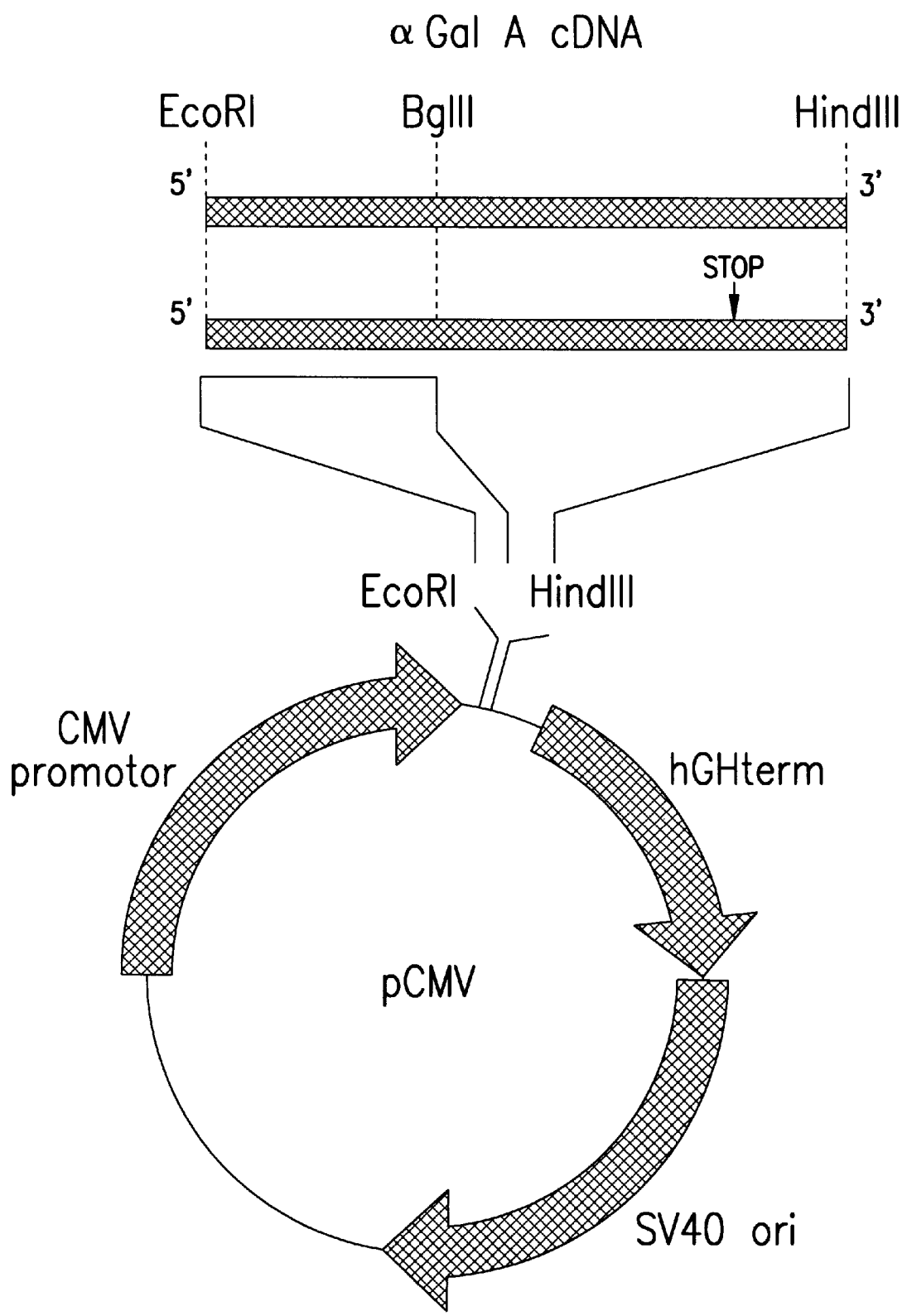
FIGS. 7A–7C. (A) Plasmid construction. Normal (wild type) or mutant (Y365X) α-Gal A cDNA was inserted into the EcoRI-HindIII cloning site of pCMV. (B) Northern blot analysis of COS-1 cells transfected with α-Gal A cDNAs. COS-1 cells were transfected with 10 μg of plasmid DNA. Three days after transfection, RNA was extracted from the cells. Ten μg of total RNA was size-fractionated by agarose gel electrophoresis and hybridized with an α-Gal A cDNA probe (upper panel), and with a β-actin cDNA probe as an internal control (lower panel). Lane 1: no transfection, lane 2: mock transfection (the vector without cDNA insertion), lane 3; pCMV-AGW (wild type cDNA), lane 4; pCMV-AGK (Y365X). © α-Gal A enzyme assay. α-Gal A activities of the cell lysates were assayed by standard methods. *P<0.05 vs. mock transfection (n=3).
Figure 7B:
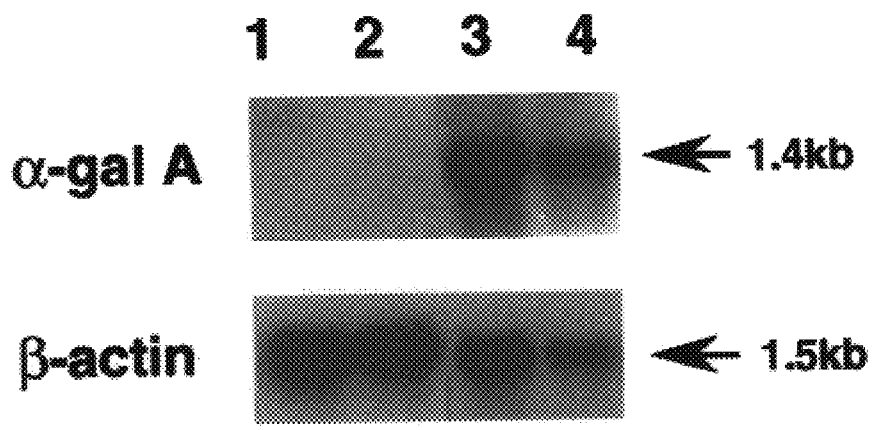
Figure 7C:
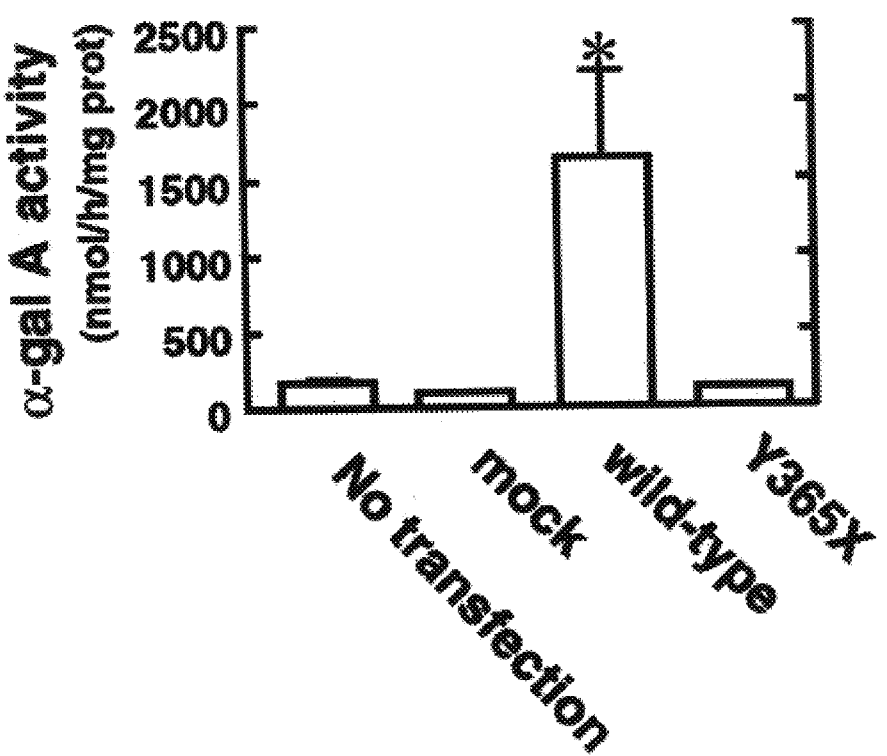

Cloning the mutant α-Gal A cDNA and expression in COS-1 cells. The expression plasmids, pCMV-AGW and pCMV-AGK, which contain the entire coding region of the wild type and mutant cDNAs of α-Gal A, respectively, were constructed as described above (FIG. 7A). Expression of the transfected α-Gal A cDNA was examined by Northern blot analysis. A very faint band of α-Gal A mRNA, which was considered to be an endogenous product of COS-1 cells, was observed in cells which had not been transfected and mock transfected cells (transfected with vector alone). Both the cells without transfection, cells transfected with pCMV-AGW or with pCMV-AGK showed distinct α-Gal A bands. There was no significant difference in the amounts of α-Gal A mRNA observed in cells transfected with pCMV-AGW or with pCMV-AGK (FIG. 7B). However, COS-1 cells transfected with pCMV-AGW showed a 16-fold increase of α-Gal A activity when compared with cells which were mock transfected, while those transfected with pCMV-AGK showed no significant increase (FIG. 7C). These results suggest that transcription of Y365X DNA is normal, but that α-Gal A activity is completely absent in this mutant.

Figure 8A:
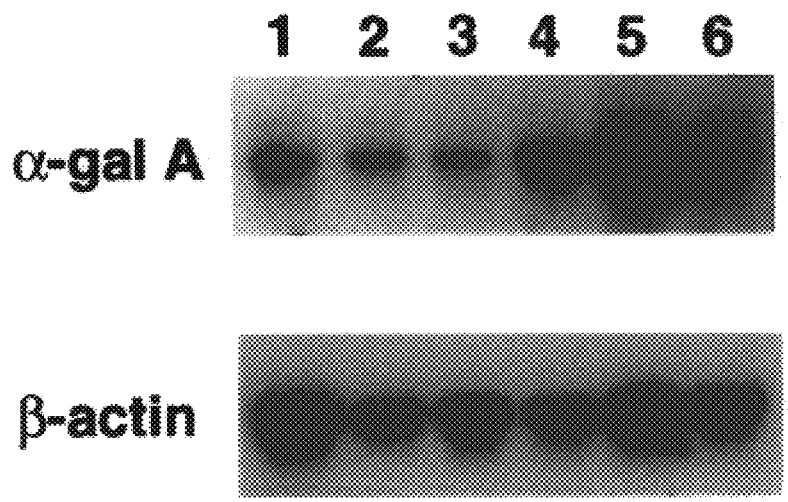
FIGS. 8A–8B. (A) Northern blot analysis of RNA from cells cotransfected with Y365X mutant and wild type α-Gal A cDNAs. Five μg of pCMV-AGW (wild type plasmid) was transfected together with either 5 μg of pCMV-AGK (Y365X mutant) or 5 μg of vector into COS-1 cells. Ten μg of total RNA prepared from the transfected cells was used for hybridization. Radioactivities of the bands were measured using Bio Image-Analyzer BA100 (Fuji Film Co., Ltd.). Lanes 1, 2 and 3 each represent an independent cotransfection with mock and wild-type plasmids. Lanes 4, 5 and 6 each represent an independent cotransfection with Y365X and wild type. (B) α-Gal A enzyme assay. The α-Gal A activities of the cell lysates from the transfections described in panel (A) were determined by subtraction of the α-Gal A activity of mock transfection, and normalization by the ratio of the wild type α-Gal A mRNA to the β-actin mRNA in the Northern blot analysis. Values represent mean±SD (as percent control of the activity in cells cotransfected with mock and wild type plasmid) for n=3.*1'<0.05.
Figure 8B:
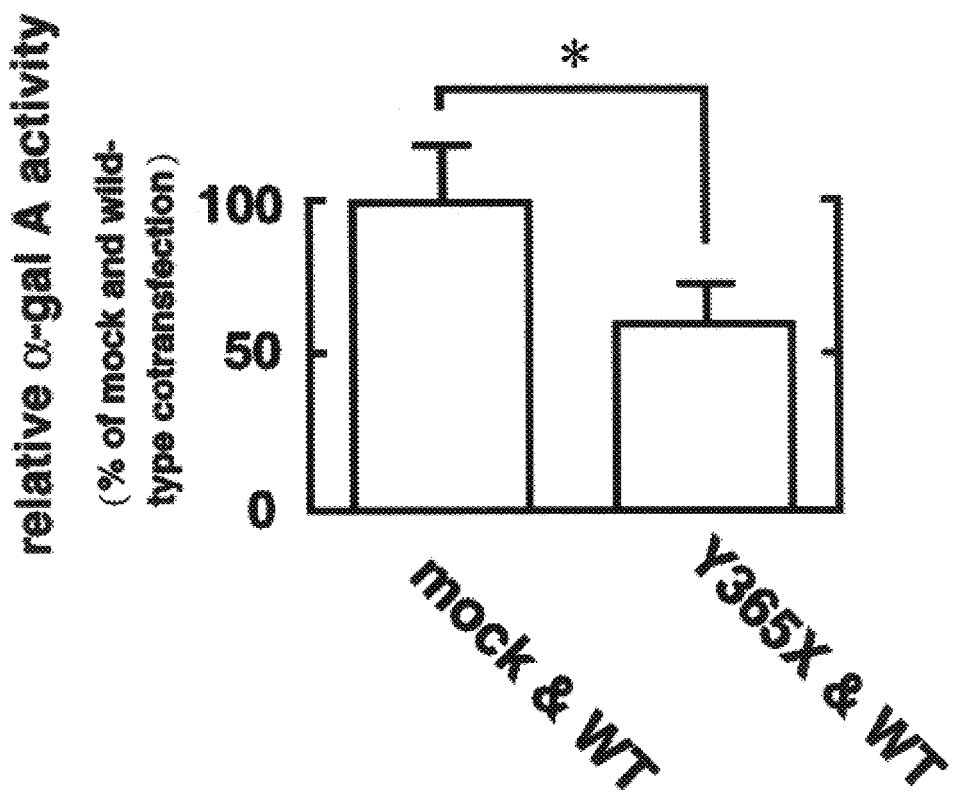

Since it is known that α-Gal A forms a homodimer in lysosomes, Y365X could have a dominant negative effect in the heterozygous genotype. To examine this possibility, COS-1 cells were transfected with 10 μg of plasmid DNA containing a 1:1 mixture of mock (control) plasmid and pCMV-AGW or a 1:1 mixture of pCMV-AGK and pCMV-AGW. The experiments were performed in triplicate for each cotransfection. The Northern blots of α-Gal A mRNA and β-actin mRNA in these cells is shown in FIG. 8). After subtraction of the α-Gal A activity of mock transfected cells and normalization with the amount of α-Gal A mRNA (with the wild type/mutant co-transfection, it was assumed that half the total α-Gal A mRNA was derived from wild type α-Gal A cDNA, and the rest was from the Y365X mutant), there was a significant decrease (about 40%) in the α-Gal A activity of cells cotransfected with wild type/mutant mixture compared with the wild type/mock plasmid mixture (FIG. 8B, P<0.05, n=3). The α-Gal A activity of cells cotransfected with pCMV-AGK and pCMV-AGW, which corrected for the total α-Gal A mRNA (including both Y365X mutant and wild type), was about 30% of that of cells cotransfected with mock plasmid and pCMV-AGW. This suggested that the mutant α-Gal A had a dominant negative effect.

Figure 9A:
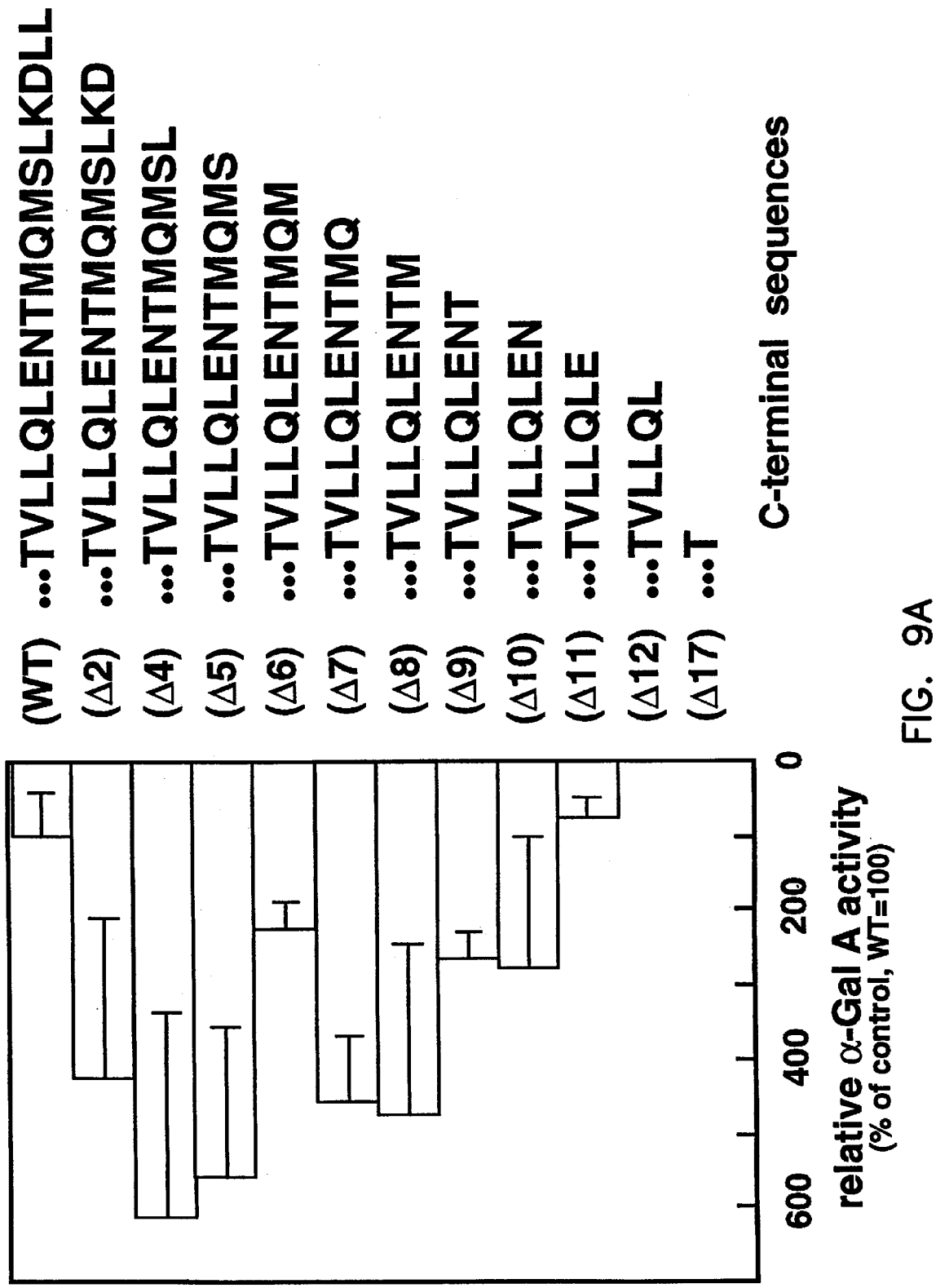
FIGS. 9A–9B. (A) Analysis of mutant cDNAs. cDNAs with premature stop codons were obtained by site-directed mutagenesis, and inserted into the EcoRI-HindIII cloning site of pCMV (see FIG. 7). The amino acid sequence of the C-terminal residues of wild type α-Gal A and truncated α-Gal A variants are shown to the right. α-Gal A activities obtained from transfected cell lysates are shown to the left. α-Gal A activity was adjusted by subtraction of activity seen after mock-transfection, and normalization by the ratio of the α-Gal A mRNA to the β-actin mRNA in the Northern blot. Values are shown as % control (wild type=100), representing mean for n=2 or 3. The amino acid sequence of wild type α-Gal A corresponds to SEQ ID NO:1; mutant Δ2 corresponds to SEQ ID NO:2; Δ4 corresponds to SEQ ID NO:3; Δ5 corresponds to SEQ ID NO:4; Δ6 corresponds to SEQ ID NO:5; Δ7 corresponds to SEQ ID NO:6; Δ8 corresponds to SEQ ID NO:7; Δ9 corresponds to SEQ ID NO:8; Δ10 corresponds to SEQ ID NO:9; Δ11 corresponds to SEQ ID NO:10; Δ12 corresponds to SEQ ID NO:11; and Δ17 corresponds to SEQ ID NO:12. (B) Northern blot analysis of α-Gal A and β-actin RNAs in cells transfected with α-Gal A expression vectors.
Figure 9B:
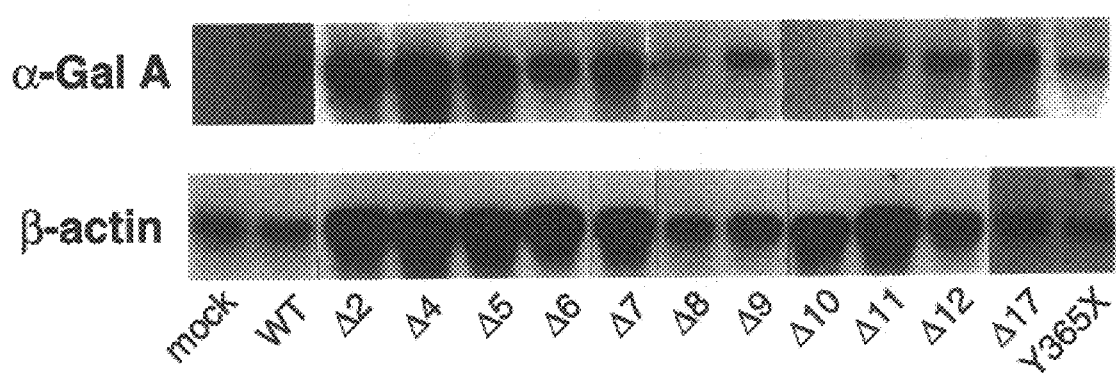

In vitro expression of the C-terminal truncated mutants. To further elucidate the function of the C-terminal region of α-Gal A, mutant α-Gal A cDNAs were constructed which resulted in various C-terminal truncations of the α-Gal A polypeptide and studied their activities in COS-1 cells. Mutant plasmids, pCMV-AGΔ2 (Δ2), pCMV-AGΔ4 (Δ4), pCMV-AGΔ5 (Δ5), pCMV-AGΔ6 (Δ6), pCMV-AGΔ7 (Δ7), pCMV-AGΔ8 (Δ8), pCMV-AGΔ9 (Δ9), PCMV-AGΔ10 (Δ10), pCMV-AGΔ11 (Δ11), pCMV-AGΔ12 (Δ12), and pCMV-AGΔ17 (Δ7), which were considered to express α-Gal A mutants lacking 2, 4, 5, 6, 7, 8, 9, 10, 11, 12, and 17 C-terminal amino acid residues, respectively, were transfected into COS-1 cells (C-terminal sequences are shown in FIG. 9A). The efficiency of each transfection was estimated by the ratio of the radioactivity of the α-Gal A mRNA band to that of the β-actin band in Northern blot, as described above (a representative autoradiogram of the Northern blot is shown in FIG. 9B).

Unexpectedly, transfections with Δ2, Δ4, Δ5, Δ6, Δ7, Δ8, Δ9, andΔ10 plasmids markedly increased α-Gal A activity in comparison with mock transfection. Moreover, even when compared with wild type, transfections with these C-terminal truncated mutants showed significant increases in enzyme activity. The α-Gal A activities observed after normalization and mock subtraction were about 420, 620, 560, 230, 460, 480, 270, and 280% of that of wild type α-Gal A with Δ2, Δ4, Δ5, Δ6, Δ7, Δ8, Δ9, and Δ10, respectively (FIG. 9A). In the transfection experiments with Δ10, α-Gal A mRNA bands in the Northern blot were faint compared with β-actin, suggesting either an abnormality in transcription or an instability of this mRNA (FIG. 9B). Transfection with Δ11 resulted in mild reduction of activity compared with wild type, and those with Δ12 and Δ17 plasmids resulted in complete reduction of α-Gal A activity (FIG. 9A).

Discussion

Interestingly, in the proband who was a heterozygous female, clinical symptoms were more severe than those seen in the usual heterozygote including cardiac involvement and hypohidrosis, of which each estimated incidence based on review of over 122 heterozygous females has been reported to be less than 1%, respectively. A few heterozygotes have previously been reported in whom the expression of the disease was comparable to that observed in severely affected hemizygous males (V. J. Ferrans et al., *Am. J. Cardiol.*, 24, 95 (1969); R. J. Desnick et al., *Surgery*, 72, 203 (1972); P. J. Rietra et al., *J. Mol. Med.*, 1, 237 (1976)). In contrast, obligate heterozygotes without any clinical manifestations and with normal levels of leukocyte α-Gal A have been reported (P. J. Rietra et al., supra; J. L. Avila et al., *Br. J. Dermat.*, 89, 149 (1973)). Such markedly variable expression is expected in females heterozygous for X-linked diseases due to random X inactivation. At the cellular level, carriers of Fabry disease have been shown to have two distinct clonal populations of cells, one with normal and the other with defective α-Gal A activity, providing evidence of random X inactivation. However, verifications of this theory in most cases have not easily been accomplished.

In order to analyze the expression of α-Gal A gene, RT-PCR direct sequencing was employed. The results of the sequencing demonstrated that the expression of the normal allele to that of the mutant allele was about 1:1 in cultured fibroblasts from the heterozygous female of the family. Lymphocyte α-Gal A activity was lower than that expected, about 30% of the normal control. This suggested that, apart from the random X chromosomal inactivation, there might be some interaction between the normal and mutant α-Gal A proteins such as heterodimerization, since this enzyme is known to exist as a homodimer (R. Kornreich et al., supra). To investigate this, equal amounts of wild type and mutant cDNAs were cotransfected into COS-1 cells. The resultant α-Gal A activity, corrected by the total α-Gal A mRNA (including both Y365X mutant and wild type), was about 30% of that of cells transfected with wild type cDNA alone (i.e., cotransfection with mock plasmid). This result could be due to an interaction between the normal and Y365X mutant α-Gal A proteins.

Several mutations of the α-Gal A gene with different C-terminal truncations have previously been reported, and all hemizygous patients with these mutations are reported to manifest a classical phenotype. However, a few mutations with single amino acid substitutions which are located in the C-terminal region are known to lead to an atypical variant in males, with manifestations limited to the heart. These findings and the characterization of the Y365X mutant suggested that the C-terminal region might carry an important functional role for α-Gal A enzymatic activity.

To examine the role of the C-terminal domain, C-terminal truncated α-Gal A polypeptides were prepared and analyzed for their enzymatic activity. Surprisingly, deletions of up to 10 amino acid residues in the extreme C terminus of α-Gal A led to a significant increase in its enzymatic activity. Deletion of the first two residues, the Leu-Leu sequence, from the C-terminal end of a α-Gal A resulted in a 4.2-fold increase in enzyme activity in COS-1 cells compared with wild type. Removal of 4, 5, 6, 7, 8, 9, and 10 amino acids induced 6.2, 5.6, 2.3, 4.6, 4.8, 2.7, and 2.8-fold increases, respectively. In transfections withΔ10, the α-Gal A mRNA band in the Northern blot was always faint compared with other mutants, suggesting either an abnormality in transcription or an instability of the mRNA. The mutant which lacks the C-terminal 11 amino acid residues (Δ11) showed a 23% reduction in enzyme activity compared with wild type. Removal of 12 (Δ12) or 17 (Δ17) C-terminal residues abolished enzyme activity in COS-1 cells. Thus, three of the mutant α-Gal A enzymes with a C-terminal truncation (Δ12, Δ17, and Δ65) had no enzymatic activity.

The data suggest that there might be some functional domain in the C-terminal sequence of the last 10 amino acid residues which inhibit enzyme activity of α-Gal A. A search of databases for sequences similar to the C terminus of α-Gal A did not identify any similar or homologous sequences, including in the sequence of α-Gal B (α-N-acetylgalactosaminidase) which is considered to have evolutionary relatedness to α-Gal A (A. M. Wang et al., *J. Biol. Chem.* 265, 21859 (1990)).

In endoplasmic reticulum resident proteins such as grp7S, disulfide isomerase, and glucose-6-phosphatase, the tetra peptide Lys-Asp-Glu-Leu (S. Munro et al., *Cell*, 48, 899 (1987)) or the Leu-Leu motif (T. Nilsson et al., *Cell*, 58, 707 (1989); M. R. Jackson et al., *EMBO J.*, 2, 3153 (1990); K. Lei et al.,*J. Clin. Invest.*, 93, 1994 (1994)) in the C-terminal domain have been identified as the specific signals for retention in endoplasmic reticulum. A conserved tripeptide Ser-Lys-Leu in the extreme C terminus of peroxisomal proteins such as rat acyl-CoA oxidase has been identified as a peroxisomal targeting sequence (S. Miyazawa et al., *Mol. Cell Biol.*, 9, 83 (1989); S. T. Gould et al., *J. Cell Biol.*, 108, 1657 (1989)). These findings, and the data described hereinabove, suggest that the C-terminal domain of some cytoplasmic proteins may contain some specific signals that regulate the protein's enzymatic function.

Therapeutic approaches using enzyme replacement are under investigation for lysosomal storage diseases, including Fabry disease. Recent success in the therapy of Gaucher's disease using mannose-terminated (macrophage-targeted) human glucocerebrosidase has demonstrated that this approach is valid (N. W. Barton et al., *Proc. Natl. Acad. Sci. USA,* 87, 1913 (1990); N. W. Barton et al., *N. Engl. J. Med.,* 324, 1464 (1991)). For Fabry disease, α-Gal A replacement using α$_2$-macroglobulin as a transport vehicle has been suggested (A. R. Tsuji et al., *J. Biochem.,* 115, 937 (1994)). As described above, removal of several residues from the C-terminal sequence of wild type α-Gal A resulted in a remarkable increase of its enzyme activity. Thus, these mutant enzymes can be used in replacement therapy, as has been done in insulin therapy using a C-terminal mutant (D. C. Howey et al., *Diabetes,* 43, 396 (1994)), and in the future, in gene therapy.

All publications and patents are incorporated by reference herein, as though individually incorporated by reference, as long as they are not inconsistent with the present disclosure. The invention is not limited to the exact details shown and described, for it should be understood that many variations and modifications may be made while remaining within the spirit and scope of the invention defined by the claims.

What is claimed is:

1. An isolated, purified α-galactosidase A polypeptide, or a variant thereof, which has a carboxy-terminal deletion of 2–11 amino acid residues and which exhibits α-galactosidase A enzyme activity.

2. The polypeptide of claim 1 corresponding to SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO: 10.

3. A therapeutic method, comprising: administering to a human at risk of, or afflicted with, Fabry disease a therapeutically amount of the polypeptide of claim 1.

4. A therapeutic method, comprising: administering to a human at risk of, or afflicted with, a condition associated with a deficiency of α-galactosidase A a therapeutically effect amount of the polypeptide of claim 1.

* * * * *

UNITED STATES PATENT AND TRADEMARK OFFICE
CERTIFICATE OF CORRECTION

PATENT NO.     : 6,210,666 B1
DATED          : April 3, 2001
INVENTOR(S)    : Miyamura It is certified that error appears in the above-identified patent and that said Letters Patent is hereby corrected as shown below:

Column 3,
Line 52, delete "111-3" and insert -- III-3 --, therefor.

Column 4,
Line 13, delete "EcoRI-Hind1I1" and insert -- EcoRI-HindIII --, therefor.
Line 48, delete "EcoRI-Hind1I1" and insert -- EcoRI-HindIII --, therefor.

Column 5,
Line 11, delete "polyA+RNA" and insert -- polyA$^+$ RNA --, therefor.

Column 8,
Line 5, delete "JMI01" and insert -- JM101 --, therefor.
Line 40, delete "JM 101" and insert -- JM101--, therefor.
Line 47, delete "ID NO:49" and insert -- ID NO:47 --, therefor.
Line 57, delete "NO.49" and insert -- NO:47 --, therefor.

Column 10,
Line 30, delete "uida" and insert -- *uidA* --, therefor.

Column 13,
Line 45, delete "omithine" and insert -- ornithine --, therefor.

Column 21,
Line 10, delete "PCMV-AGΔ7" and insert -- pCMV-AGΔ7 --, therefor.

Column 23,
Line 51, delete "C-terninal" and insert -- C-terminal --, therefor.

UNITED STATES PATENT AND TRADEMARK OFFICE
CERTIFICATE OF CORRECTION

PATENT NO.   : 6,210,666 B1
DATED        : April 3, 2001
INVENTOR(S)  : Miyamura It is certified that error appears in the above-identified patent and that said Letters Patent is hereby corrected as shown below:

<u>Column 76, claim 3,</u>
Line 3, insert -- effective -- after "therapeutically".

<u>Column 76, claim 4,</u>
Line 7, delete "effect" and insert -- effective --, therefor.

Signed and Sealed this

Thirteenth Day of November, 2001

*Attest:*

*Attesting Officer*

NICHOLAS P. GODICI
*Acting Director of the United States Patent and Trademark Office*

SEQUENCE LISTING

```
<160> NUMBER OF SEQ ID NOS: 54

<210> SEQ ID NO 1
<211> LENGTH: 398
<212> TYPE: PRT
<213> ORGANISM: Homo sapiens

<400> SEQUENCE: 1

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
```

```
                275                 280                 285
Asn Gln Asp Pro Leu Gly Lys Gln Gly Tyr Gln Leu Arg Gln Gly Asp
            290                 295                 300
Asn Phe Glu Val Trp Glu Arg Pro Leu Ser Gly Leu Ala Trp Ala Val
305                 310                 315                 320
Ala Met Ile Asn Arg Gln Glu Ile Gly Gly Pro Arg Ser Tyr Thr Ile
                325                 330                 335
Ala Val Ala Ser Leu Gly Lys Gly Val Ala Cys Asn Pro Ala Cys Phe
            340                 345                 350
Ile Thr Gln Leu Leu Pro Val Lys Arg Lys Leu Gly Phe Tyr Glu Trp
                355                 360                 365
Thr Ser Arg Leu Arg Ser His Ile Asn Pro Thr Gly Thr Val Leu Leu
            370                 375                 380
Gln Leu Glu Asn Thr Met Gln Met Ser Leu Lys Asp Leu Leu
385                 390                 395

<210> SEQ ID NO 2
<211> LENGTH: 396
<212> TYPE: PRT
<213> ORGANISM: Homo sapiens

<400> SEQUENCE: 2

Leu Asp Asn Gly Leu Ala Arg Thr Pro Thr Met Gly Trp Leu His Trp
  1               5                  10                  15
Glu Arg Phe Met Cys Asn Leu Asp Cys Gln Glu Glu Pro Asp Ser Cys
                20                  25                  30
Ile Ser Glu Lys Leu Phe Met Glu Met Ala Glu Leu Met Val Ser Glu
                35                  40                  45
Gly Trp Lys Asp Ala Gly Tyr Glu Tyr Leu Cys Ile Asp Asp Cys Trp
 50                  55                  60
Met Ala Pro Gln Arg Asp Ser Glu Gly Arg Leu Gln Ala Asp Pro Gln
 65                  70                  75                  80
Arg Phe Pro His Gly Ile Arg Gln Leu Ala Asn Tyr Val His Ser Lys
                 85                  90                  95
Gly Leu Lys Leu Gly Ile Tyr Ala Asp Val Gly Asn Lys Thr Cys Ala
                100                 105                 110
Gly Phe Pro Gly Ser Phe Gly Tyr Tyr Asp Ile Asp Ala Gln Thr Phe
            115                 120                 125
Ala Asp Trp Gly Val Asp Leu Leu Lys Phe Asp Gly Cys Tyr Cys Asp
            130                 135                 140
Ser Leu Glu Asn Leu Ala Asp Gly Tyr Lys His Met Ser Leu Ala Leu
145                 150                 155                 160
Asn Arg Thr Gly Arg Ser Ile Val Tyr Ser Cys Glu Trp Pro Leu Tyr
                165                 170                 175
Met Trp Pro Phe Gln Lys Pro Asn Tyr Thr Glu Ile Arg Gln Tyr Cys
                180                 185                 190
Asn His Trp Arg Asn Phe Ala Asp Ile Asp Asp Ser Trp Lys Ser Ile
                195                 200                 205
Lys Ser Ile Leu Asp Trp Thr Ser Phe Asn Gln Glu Arg Ile Val Asp
            210                 215                 220
Val Ala Gly Pro Gly Gly Trp Asn Asp Pro Asp Met Leu Val Ile Gly
225                 230                 235                 240
Asn Phe Gly Leu Ser Trp Asn Gln Gln Val Thr Gln Met Ala Leu Trp
                245                 250                 255
```

```
Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

Thr Ser Arg Leu Arg Ser His Ile Asn Pro Thr Gly Thr Val Leu Leu
    370                 375                 380

Gln Leu Glu Asn Thr Met Gln Met Ser Leu Lys Asp
385                 390                 395

<210> SEQ ID NO 3
<211> LENGTH: 394
<212> TYPE: PRT
<213> ORGANISM: Homo sapiens

<400> SEQUENCE: 3

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220

Val Ala Gly Pro Gly Gly Trp Asn Asp Pro Asp Met Leu Val Ile Gly
225                 230                 235                 240
```

-continued

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
            325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

Thr Ser Arg Leu Arg Ser His Ile Asn Pro Thr Gly Thr Val Leu Leu
    370                 375                 380

Gln Leu Glu Asn Thr Met Gln Met Ser Leu
385                 390

<210> SEQ ID NO 4
<211> LENGTH: 393
<212> TYPE: PRT
<213> ORGANISM: Homo sapiens

<400> SEQUENCE: 4

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
            85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
            165                 170                 175

Met Trp Pro Phe Gln Lys Pro Asn Tyr Thr Glu Ile Arg Gln Tyr Cys
        180                 185                 190

Asn His Trp Arg Asn Phe Ala Asp Ile Asp Asp Ser Trp Lys Ser Ile
    195                 200                 205

Lys Ser Ile Leu Asp Trp Thr Ser Phe Asn Gln Glu Arg Ile Val Asp

```
            210                 215                 220
Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
                260                 265                 270

Ser Pro Gln Ala Lys Ala Leu Leu Gln Asp Lys Asp Val Ile Ala Ile
                275                 280                 285

Asn Gln Asp Pro Leu Gly Lys Gln Gly Tyr Gln Leu Arg Gln Gly Asp
                290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
                340                 345                 350

Ile Thr Gln Leu Leu Pro Val Lys Arg Lys Leu Gly Phe Tyr Glu Trp
                355                 360                 365

Thr Ser Arg Leu Arg Ser His Ile Asn Pro Thr Gly Thr Val Leu Leu
370                 375                 380

Gln Leu Glu Asn Thr Met Gln Met Ser
385                 390

<210> SEQ ID NO 5
<211> LENGTH: 392
<212> TYPE: PRT
<213> ORGANISM: Homo sapiens

<400> SEQUENCE: 5

Leu Asp Asn Gly Leu Ala Arg Thr Pro Thr Met Gly Trp Leu His Trp
 1               5                  10                  15

Glu Arg Phe Met Cys Asn Leu Asp Cys Gln Glu Glu Pro Asp Ser Cys
                20                  25                  30

Ile Ser Glu Lys Leu Phe Met Glu Met Ala Glu Leu Met Val Ser Glu
                35                  40                  45

Gly Trp Lys Asp Ala Gly Tyr Glu Tyr Leu Cys Ile Asp Asp Cys Trp
50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
                100                 105                 110

Gly Phe Pro Gly Ser Phe Gly Tyr Tyr Asp Ile Asp Ala Gln Thr Phe
                115                 120                 125

Ala Asp Trp Gly Val Asp Leu Leu Lys Phe Asp Gly Cys Tyr Cys Asp
                130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
                180                 185                 190
```

-continued

```
Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

Thr Ser Arg Leu Arg Ser His Ile Asn Pro Thr Gly Thr Val Leu Leu
    370                 375                 380

Gln Leu Glu Asn Thr Met Gln Met
385                 390

<210> SEQ ID NO 6
<211> LENGTH: 391
<212> TYPE: PRT
<213> ORGANISM: Homo sapiens

<400> SEQUENCE: 6

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175
```

```
Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
            210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
            290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
                340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
            370                 375                 380

Gln Leu Glu Asn Thr Met Gln
385                 390

<210> SEQ ID NO 7
<211> LENGTH: 390
<212> TYPE: PRT
<213> ORGANISM: Homo sapiens

<400> SEQUENCE: 7

Leu Asp Asn Gly Leu Ala Arg Thr Pro Thr Met Gly Trp Leu His Trp
 1               5                  10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
 50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
            130                 135                 140

Ser Leu Glu Asn Leu Ala Asp Gly Tyr Lys His Met Ser Leu Ala Leu
```

```
            145                 150                 155                 160
Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
            210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
            245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
            290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
            325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
            370                 375                 380

Gln Leu Glu Asn Thr Met
385                 390

<210> SEQ ID NO 8
<211> LENGTH: 389
<212> TYPE: PRT
<213> ORGANISM: Homo sapiens

<400> SEQUENCE: 8

Leu Asp Asn Gly Leu Ala Arg Thr Pro Thr Met Gly Trp Leu His Trp
 1               5                  10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
            85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125
```

```
Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
    210                 215                 220

Val Ala Gly Pro Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
    275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
    370                 375                 380

Gln Leu Glu Asn Thr
385

<210> SEQ ID NO 9
<211> LENGTH: 388
<212> TYPE: PRT
<213> ORGANISM: Homo sapiens

<400> SEQUENCE: 9

Leu Asp Asn Gly Leu Ala Arg Thr Pro Thr Met Gly Trp Leu His Trp
  1               5                  10                  15

Glu Arg Phe Met Cys Asn Leu Asp Cys Gln Glu Glu Pro Asp Ser Cys
             20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
 50                  55                  60

Met Ala Pro Gln Arg Asp Ser Glu Gly Arg Leu Gln Ala Asp Pro Gln
65                   70                  75                  80

Arg Phe Pro His Gly Ile Arg Gln Leu Ala Asn Tyr Val His Ser Lys
                 85                  90                  95

Gly Leu Lys Leu Gly Ile Tyr Ala Asp Val Gly Asn Lys Thr Cys Ala
            100                 105                 110
```

-continued

```
Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

Thr Ser Arg Leu Arg Ser His Ile Asn Pro Thr Gly Thr Val Leu Leu
    370                 375                 380

Gln Leu Glu Asn
385

<210> SEQ ID NO 10
<211> LENGTH: 387
<212> TYPE: PRT
<213> ORGANISM: Homo sapiens

<400> SEQUENCE: 10

Leu Asp Asn Gly Leu Ala Arg Thr Pro Thr Met Gly Trp Leu His Trp
  1               5                  10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
```

-continued

```
                  85                  90                  95
Gly Leu Lys Leu Gly Ile Tyr Ala Asp Val Gly Asn Lys Thr Cys Ala
            100                 105                 110
Gly Phe Pro Gly Ser Phe Gly Tyr Tyr Asp Ile Asp Ala Gln Thr Phe
            115                 120                 125
Ala Asp Trp Gly Val Asp Leu Leu Lys Phe Asp Gly Cys Tyr Cys Asp
            130                 135                 140
Ser Leu Glu Asn Leu Ala Asp Gly Tyr Lys His Met Ser Leu Ala Leu
145                 150                 155                 160
Asn Arg Thr Gly Arg Ser Ile Val Tyr Ser Cys Glu Trp Pro Leu Tyr
            165                 170                 175
Met Trp Pro Phe Gln Lys Pro Asn Tyr Thr Glu Ile Arg Gln Tyr Cys
            180                 185                 190
Asn His Trp Arg Asn Phe Ala Asp Ile Asp Asp Ser Trp Lys Ser Ile
            195                 200                 205
Lys Ser Ile Leu Asp Trp Thr Ser Phe Asn Gln Glu Arg Ile Val Asp
            210                 215                 220
Val Ala Gly Pro Gly Gly Trp Asn Asp Pro Asp Met Leu Val Ile Gly
225                 230                 235                 240
Asn Phe Gly Leu Ser Trp Asn Gln Gln Val Thr Gln Met Ala Leu Trp
            245                 250                 255
Ala Ile Met Ala Ala Pro Leu Phe Met Ser Asn Asp Leu Arg His Ile
            260                 265                 270
Ser Pro Gln Ala Lys Ala Leu Leu Gln Asp Lys Asp Val Ile Ala Ile
            275                 280                 285
Asn Gln Asp Pro Leu Gly Lys Gln Gly Tyr Gln Leu Arg Gln Gly Asp
            290                 295                 300
Asn Phe Glu Val Trp Glu Arg Pro Leu Ser Gly Leu Ala Trp Ala Val
305                 310                 315                 320
Ala Met Ile Asn Arg Gln Glu Ile Gly Gly Pro Arg Ser Tyr Thr Ile
            325                 330                 335
Ala Val Ala Ser Leu Gly Lys Gly Val Ala Cys Asn Pro Ala Cys Phe
            340                 345                 350
Ile Thr Gln Leu Leu Pro Val Lys Arg Lys Leu Gly Phe Tyr Glu Trp
            355                 360                 365
Thr Ser Arg Leu Arg Ser His Ile Asn Pro Thr Gly Thr Val Leu Leu
            370                 375                 380
Gln Leu Glu
385

<210> SEQ ID NO 11
<211> LENGTH: 386
<212> TYPE: PRT
<213> ORGANISM: Homo sapiens

<400> SEQUENCE: 11

Leu Asp Asn Gly Leu Ala Arg Thr Pro Thr Met Gly Trp Leu His Trp
 1               5                  10                  15
Glu Arg Phe Met Cys Asn Leu Asp Cys Gln Glu Glu Pro Asp Ser Cys
            20                  25                  30
Ile Ser Glu Lys Leu Phe Met Glu Met Ala Glu Leu Met Val Ser Glu
            35                  40                  45
Gly Trp Lys Asp Ala Gly Tyr Glu Tyr Leu Cys Ile Asp Asp Cys Trp
            50                  55                  60
```

```
Met Ala Pro Gln Arg Asp Ser Glu Gly Arg Leu Gln Ala Asp Pro Gln
 65                  70                  75                  80

Arg Phe Pro His Gly Ile Arg Gln Leu Ala Asn Tyr Val His Ser Lys
                 85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
370                 375                 380

Gln Leu
385

<210> SEQ ID NO 12
<211> LENGTH: 381
<212> TYPE: PRT
<213> ORGANISM: Homo sapiens

<400> SEQUENCE: 12

Leu Asp Asn Gly Leu Ala Arg Thr Pro Thr Met Gly Trp Leu His Trp
 1               5                  10                  15

Glu Arg Phe Met Cys Asn Leu Asp Cys Gln Glu Glu Pro Asp Ser Cys
                 20                  25                  30

Ile Ser Glu Lys Leu Phe Met Glu Met Ala Glu Leu Met Val Ser Glu
            35                  40                  45
```

-continued

```
Gly Trp Lys Asp Ala Gly Tyr Glu Tyr Leu Cys Ile Asp Asp Cys Trp
 50                  55                  60

Met Ala Pro Gln Arg Asp Ser Glu Gly Arg Leu Gln Ala Asp Pro Gln
 65                  70                  75                  80

Arg Phe Pro His Gly Ile Arg Gln Leu Ala Asn Tyr Val His Ser Lys
                 85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr
370                 375                 380
```

<210> SEQ ID NO 13
<211> LENGTH: 22
<212> TYPE: DNA
<213> ORGANISM: Homo sapiens

<400> SEQUENCE: 13
attgttgatg ttgctggacc ag                                             22

<210> SEQ ID NO 14
<211> LENGTH: 22
<212> TYPE: DNA
<213> ORGANISM: Homo sapiens

```
<400> SEQUENCE: 14
gtcttttaat gacatctgca tt                                          22

<210> SEQ ID NO 15
<211> LENGTH: 25
<212> TYPE: DNA
<213> ORGANISM: Homo sapiens

<400> SEQUENCE: 15
gagacaactt tgaagtgaag tgtgg                                       25

<210> SEQ ID NO 16
<211> LENGTH: 23
<212> TYPE: DNA
<213> ORGANISM: Homo sapiens

<400> SEQUENCE: 16
aatgacatct gcattgtatt ttc                                         23

<210> SEQ ID NO 17
<211> LENGTH: 25
<212> TYPE: DNA
<213> ORGANISM: Homo sapiens

<400> SEQUENCE: 17
aataagtcat cggtgattgg tccgc                                       25

<210> SEQ ID NO 18
<211> LENGTH: 25
<212> TYPE: DNA
<213> ORGANISM: Homo sapiens

<400> SEQUENCE: 18
aagggaaggg agtacccaat atctg                                       25

<210> SEQ ID NO 19
<211> LENGTH: 25
<212> TYPE: DNA
<213> ORGANISM: Homo sapiens

<400> SEQUENCE: 19
cccaaggtgc ctaataaatg ggagg                                       25

<210> SEQ ID NO 20
<211> LENGTH: 25
<212> TYPE: DNA
<213> ORGANISM: Homo sapiens

<400> SEQUENCE: 20
gcttacagtc ctctgaatga acaag                                       25

<210> SEQ ID NO 21
<211> LENGTH: 25
<212> TYPE: DNA
<213> ORGANISM: Homo sapiens

<400> SEQUENCE: 21
ggtgactctt ttcctccctc tcatt                                       25

<210> SEQ ID NO 22
<211> LENGTH: 25
<212> TYPE: DNA
```

-continued

```
<213> ORGANISM: Homo sapiens

<400> SEQUENCE: 22
cctttgtggc taaatctctg gaatg                                   25

<210> SEQ ID NO 23
<211> LENGTH: 25
<212> TYPE: DNA
<213> ORGANISM: Homo sapiens

<400> SEQUENCE: 23
gccccagctg gaaattcatt tcttt                                   25

<210> SEQ ID NO 24
<211> LENGTH: 26
<212> TYPE: DNA
<213> ORGANISM: Homo sapiens

<400> SEQUENCE: 24
acagttctat tggattctgg gctcac                                  26

<210> SEQ ID NO 25
<211> LENGTH: 25
<212> TYPE: DNA
<213> ORGANISM: Homo sapiens

<400> SEQUENCE: 25
gagaaggcta caagtgcctc cttta                                   25

<210> SEQ ID NO 26
<211> LENGTH: 25
<212> TYPE: DNA
<213> ORGANISM: Homo sapiens

<400> SEQUENCE: 26
ataggaaaca agcctaccgc agggt                                   25

<210> SEQ ID NO 27
<211> LENGTH: 25
<212> TYPE: DNA
<213> ORGANISM: Homo sapiens

<400> SEQUENCE: 27
ggtttctcca tatgggtcat ctagg                                   25

<210> SEQ ID NO 28
<211> LENGTH: 25
<212> TYPE: DNA
<213> ORGANISM: Homo sapiens

<400> SEQUENCE: 28
ggcccaagac aaagttggta ttggg                                   25

<210> SEQ ID NO 29
<211> LENGTH: 25
<212> TYPE: DNA
<213> ORGANISM: Homo sapiens

<400> SEQUENCE: 29
cagggccact tatcactagt tgcta                                   25

<210> SEQ ID NO 30
<211> LENGTH: 25
```

-continued

```
<212> TYPE: DNA
<213> ORGANISM: Homo sapiens

<400> SEQUENCE: 30
ggtggacagg aagtagtagt tggca                                  25

<210> SEQ ID NO 31
<211> LENGTH: 23
<212> TYPE: DNA
<213> ORGANISM: Homo sapiens

<400> SEQUENCE: 31
ttaagcttca gtcttttaat gac                                    23

<210> SEQ ID NO 32
<211> LENGTH: 22
<212> TYPE: DNA
<213> ORGANISM: Homo sapiens

<400> SEQUENCE: 32
gtaagcttat aatgacatct gc                                     22

<210> SEQ ID NO 33
<211> LENGTH: 26
<212> TYPE: DNA
<213> ORGANISM: Homo sapiens

<400> SEQUENCE: 33
taagcttttt atgacatctg cattgt                                 26

<210> SEQ ID NO 34
<211> LENGTH: 24
<212> TYPE: DNA
<213> ORGANISM: Homo sapiens

<400> SEQUENCE: 34
taaagctttt aattacatct gcat                                   24

<210> SEQ ID NO 35
<211> LENGTH: 24
<212> TYPE: DNA
<213> ORGANISM: Homo sapiens

<400> SEQUENCE: 35
taaagctttt aatgactact gcat                                   24

<210> SEQ ID NO 36
<211> LENGTH: 27
<212> TYPE: DNA
<213> ORGANISM: Homo sapiens

<400> SEQUENCE: 36
taaagctttt aatgacatct acattgt                                27

<210> SEQ ID NO 37
<211> LENGTH: 25
<212> TYPE: DNA
<213> ORGANISM: Homo sapiens

<400> SEQUENCE: 37
ttaagcttat ctgctatgta ttttc                                  25

<210> SEQ ID NO 38
```

```
<210> SEQ ID NO 38
<211> LENGTH: 28
<212> TYPE: DNA
<213> ORGANISM: Homo sapiens

<400> SEQUENCE: 38
cataagcttt caattttcta gctgaagc                                          28

<210> SEQ ID NO 39
<211> LENGTH: 28
<212> TYPE: DNA
<213> ORGANISM: Homo sapiens

<400> SEQUENCE: 39
cataagcttt gtctattcta gctgaagc                                          28

<210> SEQ ID NO 40
<211> LENGTH: 26
<212> TYPE: DNA
<213> ORGANISM: Homo sapiens

<400> SEQUENCE: 40
gcaagctttt atagctgaag caaaac                                            26

<210> SEQ ID NO 41
<211> LENGTH: 25
<212> TYPE: DNA
<213> ORGANISM: Homo sapiens

<400> SEQUENCE: 41
ctgaagctta aacagtgcct gtggg                                             25

<210> SEQ ID NO 42
<211> LENGTH: 22
<212> TYPE: DNA
<213> ORGANISM: Homo sapiens

<400> SEQUENCE: 42
caagggtacc agcttagaca gg                                                22

<210> SEQ ID NO 43
<211> LENGTH: 1194
<212> TYPE: DNA
<213> ORGANISM: Homo sapiens

<400> SEQUENCE: 43
ctggacaatg gattggcaag gacgcctacc atgggctggc tgcactggga gcgcttcatg        60
tgcaaccttg actgccagga agagccagat tcctgcatca gtgagaagct cttcatggag       120
atggcagagc tcatggtctc agaaggctgg aaggatgcag gttatgagta cctctgcatt       180
gatgactgtt ggatggctcc ccaaagagat tcagaaggca gacttcaggc agaccctcag       240
cgctttcctc atgggattcg ccagctagct aattatgttc acagcaaagg actgaagcta       300
gggatttatg cagatgttgg aaataaaacc tgcgcaggct tccctgggag ttttggatac       360
tacgacattg atgcccagac ctttgctgac tggggagtag atctgctaaa atttgatggt       420
tgttactgtg acagtttgga aaatttggca gatggttata agcacatgtc cttggccctg       480
aataggactg gcagaagcat tgtgtactcc tgtgagtggc ctctttatat gtggccctttt       540 caaaagccca attatacaga aatccgacag tactgcaatc actggcgaaa ttttgctgac       600
attgatgatt cctggaaaag tataaagagt atcttggact ggacatcttt taaccaggag       660
agaattgttg atgttgctgg accagggggt tggaatgacc cagatatgtt agtgattggc       720
```

```
aactttggcc tcagctggaa tcagcaagta actcagatgg ccctctgggc tatcatggct      780
gctcctttat tcatgtctaa tgacctccga cacatcagcc ctcaagccaa agctctcctt      840
caggataagg acgtaattgc catcaatcag gaccccttgg gcaagcaagg gtaccagctt      900
agacagggag acaactttga agtgtgggaa cgacctctct caggcttagc ctgggctgta      960
gctatgataa accggcagga gattggtgga cctcgctctt ataccatcgc agttgcttcc     1020
ctgggtaaag gagtggcctg taatcctgcc tgcttcatca cacagctcct ccctgtgaaa     1080
aggaagctag ggttctatga atggacttca aggttaagaa gtcacataaa tcccacaggc     1140
actgttttgc ttcagctaga aaatacaatg cagatgtcat taaaagactt actt          1194

<210> SEQ ID NO 44
<211> LENGTH: 1188
<212> TYPE: DNA
<213> ORGANISM: Homo sapiens

<400> SEQUENCE: 44
ctggacaatg gattggcaag gacgcctacc atgggctggc tgcactggga gcgcttcatg       60
tgcaaccttg actgccagga agagccagat tcctgcatca gtgagaagct cttcatggag      120
atggcagagc tcatggtctc agaaggctgg aaggatgcag gttatgagta cctctgcatt      180
gatgactgtt ggatggctcc ccaaagagat tcagaaggca gacttcaggc agaccctcag      240
cgctttcctc atgggattcg ccagctagct aattatgttc acagcaaagg actgaagcta      300
gggatttatg cagatgttgg aaataaaacc tgcgcaggct ccctgggag ttttggatac      360 tacgacatta tgcccagac ctttgctgac tggggagtag atctgctaaa atttgatggt      420
tgttactgtg acagtttgga aaatttggca gatggttata agcacatgtc cttggccctg      480
aataggactg gcagaagcat tgtgtactcc tgtgagtggc ctctttatat gtggcccttt      540
caaaagccca attatacaga aatccgacag tactgcaatc actggcgaaa ttttgctgac      600
attgatgatt cctggaaaag tataaagagt atcttggact ggacatcttt taaccaggag      660
agaattgttg atgttgctgg accaggggt tggaatgacc cagatatgtt agtgattggc      720
aactttggcc tcagctggaa tcagcaagta actcagatgg ccctctgggc tatcatggct      780
gctcctttat tcatgtctaa tgacctccga cacatcagcc ctcaagccaa agctctcctt      840
caggataagg acgtaattgc catcaatcag gaccccttgg gcaagcaagg gtaccagctt      900
agacagggag acaactttga agtgtgggaa cgacctctct caggcttagc ctgggctgta      960
gctatgataa accggcagga gattggtgga cctcgctctt ataccatcgc agttgcttcc     1020
ctgggtaaag gagtggcctg taatcctgcc tgcttcatca cacagctcct ccctgtgaaa     1080
aggaagctag ggttctatga atggacttca aggttaagaa gtcacataaa tcccacaggc     1140
actgttttgc ttcagctaga aaatacaatg cagatgtcat taaaagac                 1188

<210> SEQ ID NO 45
<211> LENGTH: 1182
<212> TYPE: DNA
<213> ORGANISM: Homo sapiens

<400> SEQUENCE: 45
ctggacaatg gattggcaag gacgcctacc atgggctggc tgcactggga gcgcttcatg       60
tgcaaccttg actgccagga agagccagat tcctgcatca gtgagaagct cttcatggag      120
atggcagagc tcatggtctc agaaggctgg aaggatgcag gttatgagta cctctgcatt      180
```

-continued

```
gatgactgtt ggatggctcc ccaaagagat tcagaaggca gacttcaggc agaccctcag    240
cgctttcctc atgggattcg ccagctagct aattatgttc acagcaaagg actgaagcta    300
gggatttatg cagatgttgg aaataaaacc tgcgcaggct tccctgggag ttttggatac    360
tacgacattg atgcccagac ctttgctgac tggggagtag atctgctaaa atttgatggt    420
tgttactgtg acagtttgga aaatttggca gatggttata agcacatgtc cttggccctg    480
aataggactg gcagaagcat tgtgtactcc tgtgagtggc ctctttatat gtggcccttt    540
caaaagccca attatacaga atccgacag tactgcaatc actggcgaaa ttttgctgac     600
attgatgatt cctggaaaag tataaagagt atcttggact ggacatcttt taaccaggag    660
agaattgttg atgttgctgg accagggggt tggaatgacc cagatatgtt agtgattggc    720
aactttggcc tcagctggaa tcagcaagta actcagatgg ccctctgggc tatcatggct    780
gctcctttat tcatgtctaa tgacctccga cacatcagcc ctcaagccaa agctctcctt    840
caggataagg acgtaattgc catcaatcag gaccccttgg gcaagcaagg gtaccagctt    900
agacagggag acaactttga agtgtgggaa cgacctctct caggcttagc ctgggctgta    960
gctatgataa accggcagga gattggtgga cctcgctctt ataccatcgc agttgcttcc   1020
ctgggtaaag gagtggcctg taatcctgcc tgcttcatca cacagctcct ccctgtgaaa   1080
aggaagctag ggttctatga atggacttca aggttaagaa gtcacataaa tcccacaggc   1140
actgttttgc ttcagctaga aaatacaatg cagatgtcat ta                      1182
```

<210> SEQ ID NO 46
<211> LENGTH: 1179
<212> TYPE: DNA
<213> ORGANISM: Homo sapiens

<400> SEQUENCE: 46

```
ctggacaatg gattggcaag gacgcctacc atgggctggc tgcactggga gcgcttcatg     60
tgcaaccttg actgccagga agagccagat tcctgcatca gtgagaagct cttcatggag    120
atggcagagc tcatggtctc agaaggctgg aaggatgcag ttatgagta cctctgcatt    180 gatgactgtt ggatggctcc ccaaagagat tcagaaggca gacttcaggc agaccctcag    240
cgctttcctc atgggattcg ccagctagct aattatgttc acagcaaagg actgaagcta    300
gggatttatg cagatgttgg aaataaaacc tgcgcaggct tccctgggag ttttggatac    360
tacgacattg atgcccagac ctttgctgac tggggagtag atctgctaaa atttgatggt    420
tgttactgtg acagtttgga aaatttggca gatggttata agcacatgtc cttggccctg    480
aataggactg gcagaagcat tgtgtactcc tgtgagtggc ctctttatat gtggcccttt    540
caaaagccca attatacaga atccgacag tactgcaatc actggcgaaa ttttgctgac     600
attgatgatt cctggaaaag tataaagagt atcttggact ggacatcttt taaccaggag    660
agaattgttg atgttgctgg accagggggt tggaatgacc cagatatgtt agtgattggc    720
aactttggcc tcagctggaa tcagcaagta actcagatgg ccctctgggc tatcatggct    780
gctcctttat tcatgtctaa tgacctccga cacatcagcc ctcaagccaa agctctcctt    840
caggataagg acgtaattgc catcaatcag gaccccttgg gcaagcaagg gtaccagctt    900
agacagggag acaactttga agtgtgggaa cgacctctct caggcttagc ctgggctgta    960
gctatgataa accggcagga gattggtgga cctcgctctt ataccatcgc agttgcttcc   1020
ctgggtaaag gagtggcctg taatcctgcc tgcttcatca cacagctcct ccctgtgaaa   1080
aggaagctag ggttctatga atggacttca aggttaagaa gtcacataaa tcccacaggc   1140
```

```
actgttttgc ttcagctaga aaatacaatg cagatgtca                            1179
```

<210> SEQ ID NO 47
<211> LENGTH: 1176
<212> TYPE: DNA
<213> ORGANISM: Homo sapiens

<400> SEQUENCE: 47

```
ctggacaatg gattggcaag gacgcctacc atgggctggc tgcactggga gcgcttcatg      60
tgcaaccttg actgccagga agagccagat tcctgcatca gtgagaagct cttcatggag    120
atggcagagc tcatggtctc agaaggctgg aaggatgcag gttatgagta cctctgcatt    180
gatgactgtt ggatggctcc ccaaagagat tcagaaggca gacttcaggc agaccctcag    240
cgctttcctc atgggattcg ccagctagct aattatgttc acagcaaagg actgaagcta    300
gggatttatg cagatgttgg aaataaaacc tgcgcaggct ccctgggag ttttggatac     360
tacgacattg atgcccagac ctttgctgac tggggagtag atctgctaaa atttgatggt    420
tgttactgtg acagtttgga aaatttggca gatggttata agcacatgtc cttggccctg    480
aataggactg gcagaagcat tgtgtactcc tgtgagtggc ctctttatat gtggcccttt    540
caaaagccca attatacaga aatccgacag tactgcaatc actggcgaaa ttttgctgac    600
attgatgatt cctggaaaag tataaagagt atcttggact ggacatcttt taaccaggag    660
agaattgttg atgttgctgg accagggggt tggaatgacc cagatatgtt agtgattggc    720
aactttggcc tcagctggaa tcagcaagta actcagatgg ccctctgggc tatcatggct    780
gctcctttat tcatgtctaa tgacctccga cacatcagcc tcaagccaa agctctcctt    840
caggataagg acgtaattgc catcaatcag gaccccttgg gcaagcaagg gtaccagctt    900
agacagggag acaactttga agtgtgggaa cgacctctct caggcttagc ctgggctgta    960
gctatgataa accggcagga gattggtgga cctcgctctt ataccatcgc agttgcttcc   1020
ctgggtaaag gagtggcctg taatcctgcc tgcttcatca cacagctcct ccctgtgaaa   1080
aggaagctag ggttctatga atggacttca aggttaagaa gtcacataaa tcccacaggc   1140
actgttttgc ttcagctaga aaatacaatg cagatg                             1176
```

<210> SEQ ID NO 48
<211> LENGTH: 1173
<212> TYPE: DNA
<213> ORGANISM: Homo sapiens

<400> SEQUENCE: 48

```
ctggacaatg gattggcaag gacgcctacc atgggctggc tgcactggga gcgcttcatg      60
tgcaaccttg actgccagga agagccagat tcctgcatca gtgagaagct cttcatggag    120
atggcagagc tcatggtctc agaaggctgg aaggatgcag gttatgagta cctctgcatt    180
gatgactgtt ggatggctcc ccaaagagat tcagaaggca gacttcaggc agaccctcag    240
cgctttcctc atgggattcg ccagctagct aattatgttc acagcaaagg actgaagcta    300
gggatttatg cagatgttgg aaataaaacc tgcgcaggct ccctgggag ttttggatac     360
tacgacattg atgcccagac ctttgctgac tggggagtag atctgctaaa atttgatggt    420
tgttactgtg acagtttgga aaatttggca gatggttata agcacatgtc cttggccctg    480
aataggactg gcagaagcat tgtgtactcc tgtgagtggc ctctttatat gtggcccttt    540
caaaagccca attatacaga aatccgacag tactgcaatc actggcgaaa ttttgctgac    600
```

| | |
|---|---|
| attgatgatt cctggaaaag tataaagagt atcttggact ggacatcttt taaccaggag | 660 |
| agaattgttg atgttgctgg accagggggt tggaatgacc cagatatgtt agtgattggc | 720 |
| aactttggcc tcagctggaa tcagcaagta actcagatgg ccctctgggc tatcatggct | 780 |
| gctcctttat tcatgtctaa tgacctccga cacatcagcc ctcaagccaa agctctcctt | 840 |
| caggataagg acgtaattgc catcaatcag gaccccttgg gcaagcaagg gtaccagctt | 900 |
| agacagggag acaactttga agtgtgggaa cgacctctct caggcttagc ctgggctgta | 960 |
| gctatgataa accggcagga gattggtgga cctcgctctt ataccatcgc agttgcttcc | 1020 |
| ctgggtaaag gagtggcctg taatcctgcc tgcttcatca cacagctcct ccctgtgaaa | 1080 |
| aggaagctag ggttctatga atggacttca aggttaagaa gtcacataaa tcccacaggc | 1140 |
| actgttttgc ttcagctaga aaatacaatg cag | 1173 |

<210> SEQ ID NO 49
<211> LENGTH: 1170
<212> TYPE: DNA
<213> ORGANISM: Homo sapiens

<400> SEQUENCE: 49

| | |
|---|---|
| ctggacaatg gattggcaag gacgcctacc atgggctggc tgcactggga gcgcttcatg | 60 |
| tgcaaccttg actgccagga agagccagat tcctgcatca gtgagaagct cttcatggag | 120 |
| atggcagagc tcatggtctc agaaggctgg aaggatgcag gttatgagta cctctgcatt | 180 |
| gatgactgtt ggatggctcc ccaaagagat tcagaaggca gacttcaggc agaccctcag | 240 |
| cgctttcctc atgggattcg ccagctagct aattatgttc acagcaaagg actgaagcta | 300 |
| gggatttatg cagatgttgg aaataaaacc tgcgcaggct ccctgggag ttttggatac | 360 |
| tacgacattg atgcccagac ctttgctgac tggggagtag atctgctaaa atttgatggt | 420 |
| tgttactgtg acagtttgga aaatttggca gatggttata agcacatgtc cttggccctg | 480 |
| aataggactg gcagaagcat tgtgtactcc tgtgagtggc ctctttatat gtggcccttt | 540 |
| caaaagccca attatacaga aatccgacag tactgcaatc actggcgaaa ttttgctgac | 600 |
| attgatgatt cctggaaaag tataaagagt atcttggact ggacatcttt taaccaggag | 660 |
| agaattgttg atgttgctgg accagggggt tggaatgacc cagatatgtt agtgattggc | 720 |
| aactttggcc tcagctggaa tcagcaagta actcagatgg ccctctgggc tatcatggct | 780 |
| gctcctttat tcatgtctaa tgacctccga cacatcagcc ctcaagccaa agctctcctt | 840 |
| caggataagg acgtaattgc catcaatcag gaccccttgg gcaagcaagg gtaccagctt | 900 |
| agacagggag acaactttga agtgtgggaa cgacctctct caggcttagc ctgggctgta | 960 |
| gctatgataa accggcagga gattggtgga cctcgctctt ataccatcgc agttgcttcc | 1020 |
| ctgggtaaag gagtggcctg taatcctgcc tgcttcatca cacagctcct ccctgtgaaa | 1080 |
| aggaagctag ggttctatga atggacttca aggttaagaa gtcacataaa tcccacaggc | 1140 |
| actgttttgc ttcagctaga aaatacaatg | 1170 |

<210> SEQ ID NO 50
<211> LENGTH: 1167
<212> TYPE: DNA
<213> ORGANISM: Homo sapiens

<400> SEQUENCE: 50

| | |
|---|---|
| ctggacaatg gattggcaag gacgcctacc atgggctggc tgcactggga gcgcttcatg | 60 |
| tgcaaccttg actgccagga agagccagat tcctgcatca gtgagaagct cttcatggag | 120 |

| | |
|---|---|
| atggcagagc tcatggtctc agaaggctgg aaggatgcag gttatgagta cctctgcatt | 180 |
| gatgactgtt ggatggctcc ccaaagagat tcagaaggca gacttcaggc agaccctcag | 240 |
| cgctttcctc atgggattcg ccagctagct aattatgttc acagcaaagg actgaagcta | 300 |
| gggatttatg cagatgttgg aaataaaacc tgcgcaggct tccctgggag ttttggatac | 360 |
| tacgacattg atgcccagac ctttgctgac tggggagtag atctgctaaa atttgatggt | 420 |
| tgttactgtg acagtttgga aaatttggca gatggttata agcacatgtc cttggccctg | 480 |
| aataggactg gcagaagcat tgtgtactcc tgtgagtggc ctctttatat gtggccctt | 540 |
| caaaagccca attatacaga atccgacag tactgcaatc actggcgaaa ttttgctgac | 600 |
| attgatgatt cctggaaaag tataaagagt atcttggact ggacatcttt taaccaggag | 660 |
| agaattgttg atgttgctgg accagggggt tggaatgacc cagatatgtt agtgattggc | 720 |
| aactttggcc tcagctggaa tcagcaagta actcagatgg ccctctgggc tatcatggct | 780 |
| gctcctttat tcatgtctaa tgacctccga cacatcagcc ctcaagccaa agctctcctt | 840 |
| caggataagg acgtaattgc catcaatcag gacccctgg gcaagcaagg gtaccagctt | 900 |
| agacagggag acaactttga agtgtgggaa cgacctctct caggcttagc ctgggctgta | 960 |
| gctatgataa accggcagga gattggtgga cctcgctctt ataccatcgc agttgcttcc | 1020 |
| ctgggtaaag gagtggcctg taatcctgcc tgcttcatca cacagctcct ccctgtgaaa | 1080 |
| aggaagctag ggttctatga atggacttca aggttaagaa gtcacataaa tcccacaggc | 1140 |
| actgttttgc ttcagctaga aaataca | 1167 |

<210> SEQ ID NO 51
<211> LENGTH: 1164
<212> TYPE: DNA
<213> ORGANISM: Homo sapiens

<400> SEQUENCE: 51

| | |
|---|---|
| ctggacaatg gattggcaag gacgcctacc atgggctggc tgcactggga gcgcttcatg | 60 |
| tgcaaccttg actgccagga agagccagat tcctgcatca gtgagaagct cttcatggag | 120 |
| atggcagagc tcatggtctc agaaggctgg aaggatgcag gttatgagta cctctgcatt | 180 |
| gatgactgtt ggatggctcc ccaaagagat tcagaaggca gacttcaggc agaccctcag | 240 |
| cgctttcctc atgggattcg ccagctagct aattatgttc acagcaaagg actgaagcta | 300 |
| gggatttatg cagatgttgg aaataaaacc tgcgcaggct tccctgggag ttttggatac | 360 |
| tacgacattg atgcccagac ctttgctgac tggggagtag atctgctaaa atttgatggt | 420 |
| tgttactgtg acagtttgga aaatttggca gatggttata agcacatgtc cttggccctg | 480 |
| aataggactg gcagaagcat tgtgtactcc tgtgagtggc ctctttatat gtggccctt | 540 |
| caaaagccca attatacaga atccgacag tactgcaatc actggcgaaa ttttgctgac | 600 |
| attgatgatt cctggaaaag tataaagagt atcttggact ggacatcttt taaccaggag | 660 |
| agaattgttg atgttgctgg accagggggt tggaatgacc cagatatgtt agtgattggc | 720 |
| aactttggcc tcagctggaa tcagcaagta actcagatgg ccctctgggc tatcatggct | 780 |
| gctcctttat tcatgtctaa tgacctccga cacatcagcc ctcaagccaa agctctcctt | 840 |
| caggataagg acgtaattgc catcaatcag gacccctgg gcaagcaagg gtaccagctt | 900 |
| agacagggag acaactttga agtgtgggaa cgacctctct caggcttagc ctgggctgta | 960 |
| gctatgataa accggcagga gattggtgga cctcgctctt ataccatcgc agttgcttcc | 1020 |

```
ctgggtaaag gagtggcctg taatcctgcc tgcttcatca cacagctcct ccctgtgaaa    1080
aggaagctag ggttctatga atggacttca aggttaagaa gtcacataaa tcccacaggc    1140
actgttttgc ttcagctaga aaat                                            1164

<210> SEQ ID NO 52
<211> LENGTH: 1161
<212> TYPE: DNA
<213> ORGANISM: Homo sapiens

<400> SEQUENCE: 52
ctggacaatg gattggcaag gacgcctacc atgggctggc tgcactggga gcgcttcatg      60
tgcaaccttg actgccagga agagccagat tcctgcatca gtgagaagct cttcatggag     120
atggcagagc tcatggtctc agaaggctgg aaggatgcag gttatgagta cctctgcatt     180
gatgactgtt ggatggctcc ccaaagagat tcagaaggca gacttcaggc agaccctcag     240
cgctttcctc atgggattcg ccagctagct aattatgttc acagcaaagg actgaagcta     300
gggatttatg cagatgttgg aaataaaacc tgcgcaggct tccctgggag ttttggatac     360
tacgacattg atgcccagac ctttgctgac tggggagtag atctgctaaa atttgatggt     420
tgttactgtg acagtttgga aaatttggca gatggttata agcacatgtc cttggccctg     480
aataggactg gcagaagcat tgtgtactcc tgtgagtggc ctctttatat gtggccttt      540 caaaagccca attatacaga aatccgacag tactgcaatc actggcgaaa ttttgctgac     600
attgatgatt cctggaaaag tataaagagt atcttggact ggacatcttt taaccaggag     660
agaattgttg atgttgctgg accagggggt tggaatgacc cagatatgtt agtgattggc     720
aactttggcc tcagctggaa tcagcaagta actcagatgg ccctctgggc tatcatggct     780
gctcctttat tcatgtctaa tgacctccga cacatcagcc tcaagccaa agctctcctt     840 caggataagg acgtaattgc catcaatcag gaccccttgg gcaagcaagg gtaccagctt     900
agacagggag acaactttga agtgtgggaa cgacctctct caggcttagc ctgggctgta     960
gctatgataa accggcagga gattggtgga cctcgctctt ataccatcgc agttgcttcc    1020
ctgggtaaag gagtggcctg taatcctgcc tgcttcatca cacagctcct ccctgtgaaa    1080
aggaagctag ggttctatga atggacttca aggttaagaa gtcacataaa tcccacaggc    1140
actgttttgc ttcagctaga a                                              1161

<210> SEQ ID NO 53
<211> LENGTH: 1158
<212> TYPE: DNA
<213> ORGANISM: Homo sapiens

<400> SEQUENCE: 53
ctggacaatg gattggcaag gacgcctacc atgggctggc tgcactggga gcgcttcatg      60
tgcaaccttg actgccagga agagccagat tcctgcatca gtgagaagct cttcatggag     120
atggcagagc tcatggtctc agaaggctgg aaggatgcag gttatgagta cctctgcatt     180
gatgactgtt ggatggctcc ccaaagagat tcagaaggca gacttcaggc agaccctcag     240
cgctttcctc atgggattcg ccagctagct aattatgttc acagcaaagg actgaagcta     300
gggatttatg cagatgttgg aaataaaacc tgcgcaggct tccctgggag ttttggatac     360
tacgacattg atgcccagac ctttgctgac tggggagtag atctgctaaa atttgatggt     420
tgttactgtg acagtttgga aaatttggca gatggttata agcacatgtc cttggccctg     480
aataggactg gcagaagcat tgtgtactcc tgtgagtggc ctctttatat gtggccttt      540
```

```
caaaagccca attatacaga aatccgacag tactgcaatc actggcgaaa ttttgctgac      600
attgatgatt cctggaaaag tataaagagt atcttggact ggacatcttt taaccaggag      660
agaattgttg atgttgctgg accagggggt tggaatgacc cagatatgtt agtgattggc      720
aactttggcc tcagctggaa tcagcaagta actcagatgg ccctctgggc tatcatggct      780
gctcctttat tcatgtctaa tgacctccga cacatcagcc ctcaagccaa agctctcctt      840
caggataagg acgtaattgc catcaatcag gacccctttgg gcaagcaagg gtaccagctt     900
agacagggag acaactttga agtgtgggaa cgacctctct caggcttagc ctgggctgta     960
gctatgataa accggcagga gattggtgga cctcgctctt ataccatcgc agttgcttcc    1020
ctgggtaaag gagtggcctg taatcctgcc tgcttcatca cacagctcct ccctgtgaaa    1080
aggaagctag ggttctatga atggacttca aggttaagaa gtcacataaa tcccacaggc    1140
actgttttgc ttcagcta                                                  1158

<210> SEQ ID NO 54
<211> LENGTH: 1155
<212> TYPE: DNA
<213> ORGANISM: Homo sapiens

<400> SEQUENCE: 54
ctggacaatg gattggcaag gacgcctacc atgggctggc tgcactggga gcgcttcatg       60
tgcaaccttg actgccagga agagccagat tcctgcatca gtgagaagct cttcatggag      120
atggcagagc tcatggtctc agaaggctgg aaggatgcag gttatgagta cctctgcatt      180
gatgactgtt ggatggctcc ccaaagagat tcagaaggca gacttcaggc agaccctcag      240
cgctttcctc atgggattcg ccagctagct aattatgttc acagcaaagg actgaagcta      300
gggatttatg cagatgttgg aaataaaacc tgcgcaggct ccctgggag ttttggatac      360 tacgacattg atgcccagac ctttgctgac tggggagtag atctgctaaa atttgatggt      420
tgttactgtg acagtttgga aaatttggca gatggttata agcacatgtc cttggccctg      480
aataggactg gcagaagcat tgtgtactcc tgtgagtggc ctctttatat gtggccattt      540
caaaagccca attatacaga aatccgacag tactgcaatc actggcgaaa ttttgctgac      600
attgatgatt cctggaaaag tataaagagt atcttggact ggacatcttt taaccaggag      660
agaattgttg atgttgctgg accagggggt tggaatgacc cagatatgtt agtgattggc      720
aactttggcc tcagctggaa tcagcaagta actcagatgg ccctctgggc tatcatggct      780
gctcctttat tcatgtctaa tgacctccga cacatcagcc ctcaagccaa agctctcctt      840
caggataagg acgtaattgc catcaatcag gacccctttgg gcaagcaagg gtaccagctt     900
agacagggag acaactttga agtgtgggaa cgacctctct caggcttagc ctgggctgta     960
gctatgataa accggcagga gattggtgga cctcgctctt ataccatcgc agttgcttcc    1020
ctgggtaaag gagtggcctg taatcctgcc tgcttcatca cacagctcct ccctgtgaaa    1080
aggaagctag ggttctatga atggacttca aggttaagaa gtcacataaa tcccacaggc    1140
actgttttgc ttcag                                                     1155
```